(12) United States Patent
Hwang et al.

(10) Patent No.: US 7,842,310 B2
(45) Date of Patent: Nov. 30, 2010

(54) PHARMACEUTICAL COMPOSITIONS IN PARTICULATE FORM

(75) Inventors: Robin Hwang, Cary, NC (US); Vincent Sullivan, Cary, NC (US); Juan Huang, Cary, NC (US); Zhaolin Wang, Edmonton (CA); John A. Mikszta, Durham, NC (US); David Montgomery, Cary, NC (US); Brandi Ford, Apex, NC (US); Anjana Bhuta-Wills, Cary, NC (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1392 days.

(21) Appl. No.: 10/299,012

(22) Filed: Nov. 19, 2002

(65) Prior Publication Data

US 2003/0180755 A1 Sep. 25, 2003

Related U.S. Application Data

(60) Provisional application No. 60/419,959, filed on Oct. 22, 2002, provisional application No. 60/339,156, filed on Dec. 11, 2001, provisional application No. 60/331,952, filed on Nov. 19, 2001.

(51) Int. Cl.
*A61K 9/19* (2006.01)
*F26B 5/04* (2006.01)
*F26B 5/06* (2006.01)
*F26B 5/00* (2006.01)

(52) U.S. Cl. .......................... 424/489; 34/285; 34/286; 34/298; 34/284; 159/3; 424/209.1; 424/499

(58) Field of Classification Search .............. 435/235.1, 435/236, 239, 320.1, 283.1, 289.1
See application file for complete search history.

(56) References Cited

U.S. PATENT DOCUMENTS

| | | |
|---|---|---|
| 2,798,835 A | 7/1957 | Markham et al. |
| 2,946,724 A | 7/1960 | Valentine |
| 3,313,032 A | 4/1967 | Malecki |
| 3,513,559 A | 5/1970 | Eilenberg |
| 3,594,471 A | 7/1971 | Hertzberger et al. |
| 3,608,066 A | 9/1971 | Illartein |
| 3,634,582 A | 1/1972 | Hartley et al. |
| 3,755,557 A | 8/1973 | Jacobs et al. |
| 3,932,943 A | 1/1976 | Briggs et al. |
| 3,957,965 A | 5/1976 | Hartley et al. |
| 4,036,223 A | 7/1977 | Obert |
| 4,251,509 A | 2/1981 | Hanson et al. |
| 4,323,478 A | 4/1982 | Adams et al. |
| 4,329,332 A | 5/1982 | Couvreur et al. |
| 4,432,969 A | 2/1984 | Batchelor |
| 4,608,764 A | 9/1986 | Leuenberger |
| 4,613,500 A | 9/1986 | Suzuki et al. |
| 4,962,091 A | 10/1990 | Eppstein et al. |
| 4,985,242 A | 1/1991 | Sekine et al. |
| 5,075,109 A | 12/1991 | Tice et al. |
| 5,204,108 A | 4/1993 | Illum |
| 5,208,998 A * | 5/1993 | Oyler, Jr. ..................... 34/288 |
| 5,254,330 A | 10/1993 | Ganderton et al. |
| 5,354,562 A | 10/1994 | Platz et al. |
| 5,628,993 A | 5/1997 | Yamagata et al. |
| 5,665,383 A | 9/1997 | Grinstaff et al. |
| 5,690,954 A | 11/1997 | Illum |
| 5,750,100 A | 5/1998 | Yamagata et al. |
| 5,756,104 A | 5/1998 | de Haan et al. |
| 5,804,212 A | 9/1998 | Illum |
| 5,814,344 A | 9/1998 | Tice et al. |
| 5,853,763 A | 12/1998 | Tice et al. |
| 5,855,913 A | 1/1999 | Hanes et al. |
| 5,874,064 A | 2/1999 | Edwards et al. |
| 5,902,565 A | 5/1999 | Cox et al. |
| 5,908,825 A | 6/1999 | Fasano et al. |

(Continued)

FOREIGN PATENT DOCUMENTS

WO WO 90/13285 A 11/1990

(Continued)

OTHER PUBLICATIONS

Maa et al. Biotech and Bioeng. 1998 vol. 60 pp. 301309.*

(Continued)

*Primary Examiner*—Mary E Mosher
*Assistant Examiner*—Myron G Hill
(74) *Attorney, Agent, or Firm*—Alston & Bird LLP

(57) ABSTRACT

A method of preparing a pharmaceutical composition is described, comprising 1) atomizing a liquid formulation of a therapeutic agent to produce an atomized formulation; 2) freezing said atomized formulation to form solid particles; and 3) drying said solid particles at about atmospheric pressure to produce a powder, wherein said drying is performed in the presence of vibration, internals, mechanical stirring, or a combination thereof. Another method is described, comprising 1) atomizing a liquid formulation of a therapeutic agent to produce an atomized formulation; 2) freezing said atomized formulation to form solid particles; and 3) drying said solid particles to produce a powder; wherein the atomized formulation comprises droplets having an average mean diameter of between about 35μ and about 300μ, and/or the powder comprises dried particles having an average mean diameter of between about 35μ and about 300μ. Compositions made by the above methods, and methods of using the compositions, are also described.

23 Claims, 23 Drawing Sheets

U.S. PATENT DOCUMENTS

| | | | |
|---|---|---|---|
| 5,916,597 A | 6/1999 | Lee et al. | |
| 5,942,242 A | 8/1999 | Mizushima et al. | |
| 5,952,008 A | 9/1999 | Bäckström et al. | |
| 5,981,719 A | 11/1999 | Woiszwillo et al. | |
| 5,985,309 A | 11/1999 | Edwards et al. | |
| 6,004,574 A | 12/1999 | Bäckström et al. | |
| 6,024,983 A | 2/2000 | Tice et al. | |
| 6,098,619 A | 8/2000 | Britto et al. | |
| 6,136,295 A | 10/2000 | Edwards et al. | |
| 6,136,606 A | 10/2000 | Chatfield | |
| 6,168,587 B1 | 1/2001 | Bellhouse et al. | |
| RE37,053 E | 2/2001 | Hanes et al. | |
| 6,254,854 B1 | 7/2001 | Edwards et al. | |
| 6,284,282 B1* | 9/2001 | Maa et al. | 424/499 |
| 6,290,962 B1 | 9/2001 | Michetti et al. | |
| 6,294,153 B1 | 9/2001 | Modi | |
| 6,309,623 B1 | 10/2001 | Weers et al. | |
| 6,328,967 B1 | 12/2001 | Rivera | |
| 6,391,318 B1 | 5/2002 | Illum et al. | |
| 6,399,102 B1 | 6/2002 | Edwards et al. | |
| 6,436,443 B2 | 8/2002 | Edwards et al. | |
| 6,447,752 B2 | 9/2002 | Edwards et al. | |
| 6,447,753 B2 | 9/2002 | Edwards et al. | |
| 6,475,468 B2 | 11/2002 | Zhu et al. | |
| 6,479,049 B1 | 11/2002 | Platz et al. | |
| 6,485,707 B2 | 11/2002 | Zhu et al. | |
| 6,503,480 B1 | 1/2003 | Edwards et al. | |
| 6,503,481 B1 | 1/2003 | Thurston et al. | |
| 6,521,597 B1 | 2/2003 | Vickery et al. | |
| 6,534,065 B1 | 3/2003 | Makin et al. | |
| 6,537,265 B2 | 3/2003 | Thanavala et al. | |
| 6,544,497 B2 | 4/2003 | Zhu et al. | |
| 6,551,578 B2 | 4/2003 | Adjei et al. | |
| 6,551,622 B1 | 4/2003 | Jackson | |
| 6,558,961 B1 | 5/2003 | Sarphie et al. | |
| 6,562,352 B1 | 5/2003 | Roberts et al. | |
| 6,565,871 B2 | 5/2003 | Roser et al. | |
| 6,565,888 B1 | 5/2003 | Tracy et al. | |
| 6,569,406 B2 | 5/2003 | Stevenson et al. | |
| 6,584,782 B2 | 7/2003 | Leuenberger et al. | |
| 6,585,957 B1 | 7/2003 | Adjei et al. | |
| 6,586,008 B1 | 7/2003 | Batycky et al. | |
| 2001/0018056 A1 | 8/2001 | Roberts | |
| 2001/0033828 A1 | 10/2001 | Edwards et al. | |
| 2001/0033829 A1 | 10/2001 | Edwards et al. | |
| 2001/0033830 A1 | 10/2001 | Edwards et al. | |
| 2001/0038858 A1 | 11/2001 | Roser et al. | |
| 2001/0053368 A1 | 12/2001 | Burt et al. | |
| 2002/0009418 A1 | 1/2002 | Steiner et al. | |
| 2002/0009463 A1 | 1/2002 | Raa et al. | |
| 2002/0034514 A1 | 3/2002 | Rivera | |
| 2002/0041867 A1 | 4/2002 | Jones et al. | |
| 2002/0061336 A1 | 5/2002 | O'Connor et al. | |
| 2002/0110525 A1 | 8/2002 | Adjei et al. | |
| 2002/0110526 A1 | 8/2002 | Zhu et al. | |
| 2002/0110527 A1 | 8/2002 | Zhu et al. | |
| 2002/0110528 A1 | 8/2002 | Zhu et al. | |
| 2002/0119117 A1 | 8/2002 | Zhu et al. | |
| 2002/0120228 A1 | 8/2002 | Maa et al. | |
| 2002/0128179 A1 | 9/2002 | Tacon et al. | |
| 2002/0141947 A1 | 10/2002 | Edwards et al. | |
| 2002/0146373 A1 | 10/2002 | Edwards et al. | |
| 2002/0159954 A1 | 10/2002 | Small et al. | |
| 2002/0198510 A1 | 12/2002 | Thanavala et al. | |
| 2003/0007979 A1 | 1/2003 | Chatfield et al. | |
| 2003/0009149 A1 | 1/2003 | Thanavala et al. | |
| 2003/0012742 A1 | 1/2003 | Edwards et al. | |
| 2003/0035776 A1 | 2/2003 | Hodges et al. | |
| 2003/0039665 A1 | 2/2003 | Illum et al. | |
| 2003/0044771 A1 | 3/2003 | Anderson et al. | |
| 2003/0064033 A1 | 4/2003 | Brown et al. | |
| 2003/0091592 A1 | 5/2003 | Barber | |
| 2003/0096259 A1 | 5/2003 | McCarthy et al. | |
| 2003/0099668 A1 | 5/2003 | Bachmann et al. | |
| 2003/0113272 A1 | 6/2003 | Staniforth | |
| 2003/0118513 A1 | 6/2003 | Basu et al. | |
| 2003/0119183 A1 | 6/2003 | Groner | |
| 2003/0129139 A1 | 7/2003 | Batycky et al. | |
| 2003/0133879 A1 | 7/2003 | Martyn | |
| 2003/0133934 A1 | 7/2003 | Leserman et al. | |
| 2003/0186271 A1* | 10/2003 | Hwang et al. | 435/6 |
| 2004/0213745 A1* | 10/2004 | Sullivan et al. | 424/46 |

FOREIGN PATENT DOCUMENTS

| | | |
|---|---|---|
| WO | WO 95/24183 A1 | 9/1995 |
| WO | WO 97/20576 A | 6/1997 |
| WO | WO 00/45792 A | 8/2000 |
| WO | WO 01/63191 A | 8/2001 |
| WO | WO 01/64188 A | 9/2001 |
| WO | WO 01/93829 A | 12/2001 |
| WO | WO 02/060411 A2 | 8/2002 |
| WO | WO 02/101412 A | 12/2002 |
| WO | WO 03/086443 A | 10/2003 |

OTHER PUBLICATIONS

Geldart (1973 Powder Tech 7, pp. 285-292).*
Takeuchi, et al, Enteral Absorption of Insulin in Rats from Mucoadhesive Chitosan-Coated Liposomes, Pharmaceutical Research, vol. 13, Issue 6, Jun. 1996, pp. 896-901.*
Macklin, et al., Immunization of Pigs with a Partide-Mediated DNA Vaccine to Influenza A Virus Protects against Challenge with Homologous Virus J. Virol. 1998 72: 1491-1496.*
Carrasquillo, et al., "Reduct. Of Struct. Pertubations in Bovine Serum Albumin by non-Acqueous Microencapsulation," *J. of Pharm. And Pharmacol.*, 2001, pp. 115-120, vol. 53(1).
Maa, Y-F., et al., "Protein Inhalation Powders: Spray Drying vs. Spray Freeze Drying," *Pharma. Res.*, 1999, pp. 249-254, vol. 16(2).
Maa, Y-F., et al., "Biopharma. Powders: Particle Formulation Considerations," *Current Pharmaceutical Biotechnology*, Bentham Sci. Pub., 2003, pp. 283-302, vol. 1(3).
Ramshaw, I.A., The Prime-Boost Strategy: Exciting Prospects for Improved Vaccination, *Immun. Today*, pp. 163-165, vol. 21(4).
Mumenthalur, M. and H. Leuenberger, "Atmospheric Spray-Freeze Drying: A Suitable Alternative in Freeze-Drying Technology," *International Journal of Pharmaceutics*, 1991 pp. 97-110, vol. 72.
Supplementary European Search Report for European Application No. EP 02 80 6904, dated Nov. 28, 2005.
Mumenthaler, M. and H. Leuenberger, "Atmospheric Spray-Freeze Drying: A Suitable Alternative in Freeze-Drying Technology," *International Journal of Pharmaceutics*, 1991, pp. 97-110, vol. 72.
Bosquillon et al., "Influence of formulation excipients and physical characteristics of inhalation dry powders on their aerosolization performance", Journal of Controlled Release 70, pp. 329-339, (2001).
Shekunov et al., "Crystallization processes in pharmaceutical technology and drug delivery design", Journal of Crystal Growth 211, pp. 122-136 (2000).
Phipps et al., "Application of isothermal microcalorimetry in solid state drug development", PSTT vol. 3, No. 1, pp. 9-17 (2000).
Jung et al., "Particle design using supercritical fluids: Literature and patent survey", Journal of Supercritical Fluids 20, pp. 179-219. (2001).
Hu et al., "Improvement of Dissolution Rates of Poorly Water Soluble APIs Using Novel Spray Freezing into Liquid Technology", Pharmaceutical Research, vol. 19, No. 9, pp. 1278-1284. (2002).
Robinson et al., "DNA Vaccines: A New Approach to Immunization", in Vaccines 95, Chanock et al., eds., Cold Spring Harbor Laboratory Press,Cold Spring Harbor, N.Y., pp. 69-75, (1995).
Elia et al., "Intensification of transfer fluxes and control of product properties in freeze-drying", Chemical Engineering and Processing 37, pp. 347-358, (1998).

Yu, Amorphous pharmaceutical solids: preparation, characterization and stabilization, Advanced Drug Delivery Reviews, 48, pp. 27-42, (2001).

D. Geldart, "The Effect of Particle Size and Size Distribution on the Behaviour of Gas-Fluidised Beds", Powder Technology 6, pp. 201-215, (1972).

Liu et al., "Fundamental and practical developments of magnetofluidized beds: a review", Powder Technology, 64, pp. 3-41, (1991).

Mori et al., "Vibro-Fluidization of Group-C Particles and its Industrial Applications", Advances in Fluidization Engineering 276, pp. 88-94, vol. 86.

Dutta et al., "Effects of External Vibration and the Addition of Fibers on the Fluidization of a Fine Powder", Advances in Fluidized Systems, 281, vol. 87, pp. 38-46.

E. Geldart, "Types of Gas Fluidization", Powder Technology 7, pp. 285-292. (1973).

J. Visser, "An Invited Review, Van der Waals and Other Cohesive Forces Affecting Powder Fluidization", Powder Technology 58, pp. 1-10, (1989).

Parker et al., "Control-relevant modeling in drug delivery", Advanced Drug Delivery Reviews 48, pp. 211-228, (2001).

* cited by examiner

SD: Spray Dry    SFD: Spray Freeze Dry

PHARMACEUTICAL COMPOSITIONS IN PARTICULATE FORM

This application claims priority to U.S. provisional application No. 60/419,959, filed Oct. 22, 2002, U.S. provisional application No. 60/339,156, filed Dec. 11, 2001 and U.S. provisional application No. 60/331,952, filed Nov. 19, 2001, each of which is hereby incorporated by reference in its entirety.

BACKGROUND

1. Field of the Invention

The present invention relates, e.g., to methods of preparing dried pharmaceutical compositions, in particulate (e.g., in powder) form. Such compositions are suitable for administration to, e.g., mucosal tissues (e.g., following intranasal administration). Compositions prepared by the methods of the invention, and methods of administering the compositions to a patient, are also described. Exemplary inventive compositions include insulin, and influenza ("flu") vaccines comprising inactivated viral particles or a nucleic acid encoding influenza haemagglutinin.

2. Background Information

Methods have been reported for formulating dried pharmaceutical compositions. These methods include, e.g., steps of precipitation, spray-drying, and/or mechanical milling of dried substances. Some of the reported methods utilize non-aqueous solvents to provide rapid moisture evaporation and to reduce processing time. Such solvents can damage the pharmaceutical agents (e.g., proteins) being dried. Particles produced by the reported methods often exhibit a tendency to agglomerate, and/or lack a suitable size, density (e.g., tap density), morphology and/or stability for optimal pharmaceutical use.

There is a need for methods to produce dried pharmaceutical compositions that lack one or more, or other, of the above-mentioned drawbacks.

SUMMARY OF THE INVENTION

The present application relates, e.g., to a method of preparing a pharmaceutical composition in the form of a powder, comprising drying the composition at about atmospheric pressure in the presence of, e.g., vibration, internals, mechanical stirring, or a combination thereof. In another embodiment, the invention relates, e.g., to a method of preparing a pharmaceutical composition in particulate form, (e.g., in the form of a powder), wherein, e.g., the powder comprises dried particles having an average mean diameter of between about 35 μm and about 100 μm. Compositions made by the above methods, and methods of using the compositions, are also described.

BRIEF DESCRIPTION OF THE DRAWINGS

Various features and attendant advantages of the present invention will be more fully appreciated as the same becomes better understood when considered in conjunction with the accompanying drawings.

| 16. | SFD chamber | 36. | Pump |
|---|---|---|---|
| 2. | Spray nozzle | 20. | Cooling system |
| 48. | Heating tape | 44. | By-pass valve |
| 12. | Solution (liq.) | 46. | By-pass line |
| 28. | Filter | 18. | Nebulizing air |
| 38. | Valve | 49. | Vibration source |
| 32. | Air Filter | 50. | Internals |

Figure 2:
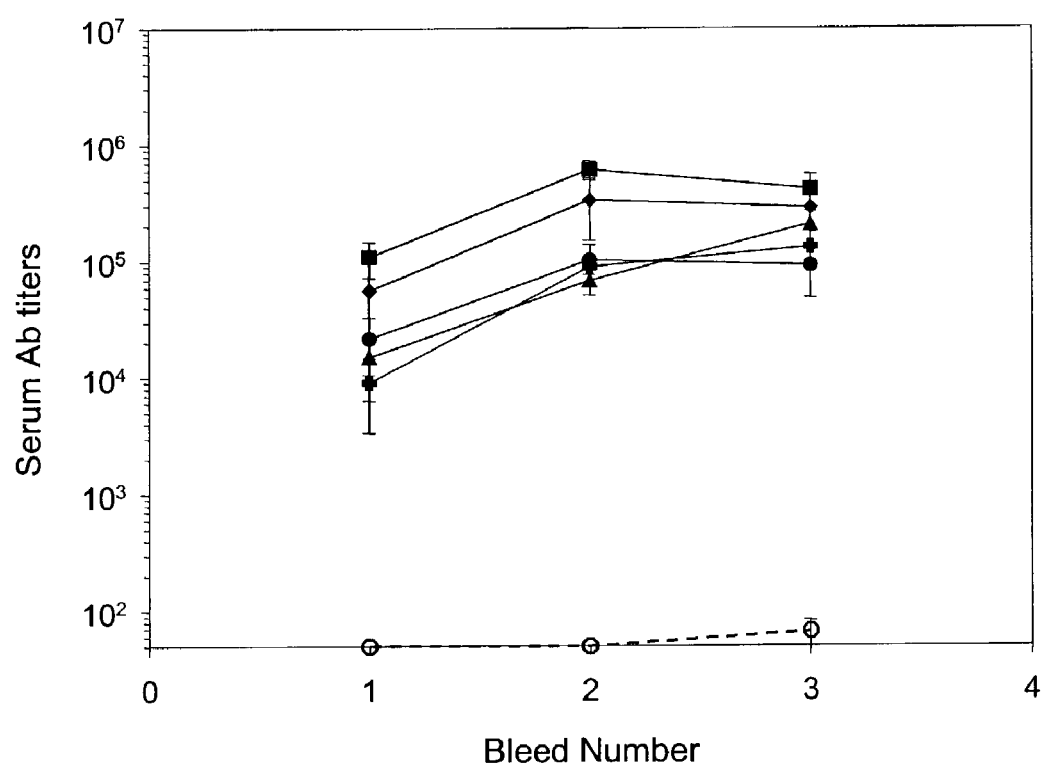

FIG. 2 shows the serum antibody (Ab) response following IN delivery of various flu vaccine formulations.

Figure 3:
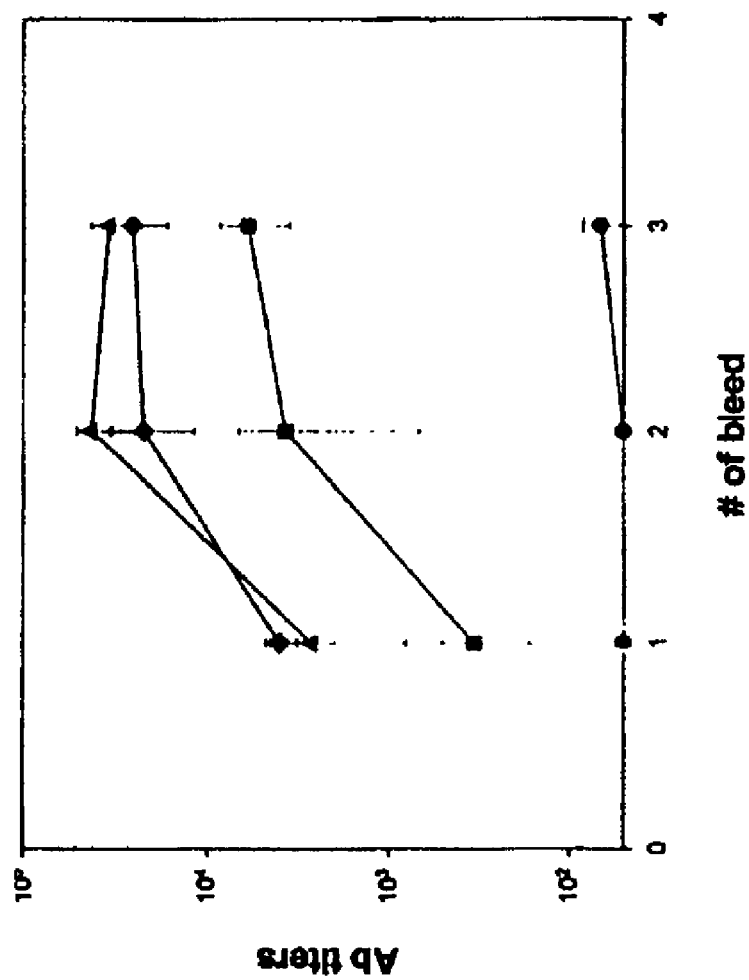

- IN flu liquid
- I
- IN FD
- IN FD powder/chitosan
- IN SFD powder/chitosan
- trehalose only FIG. 3 shows the serum Ab response rats following immunization with pFLU-HA.

Figure 4:
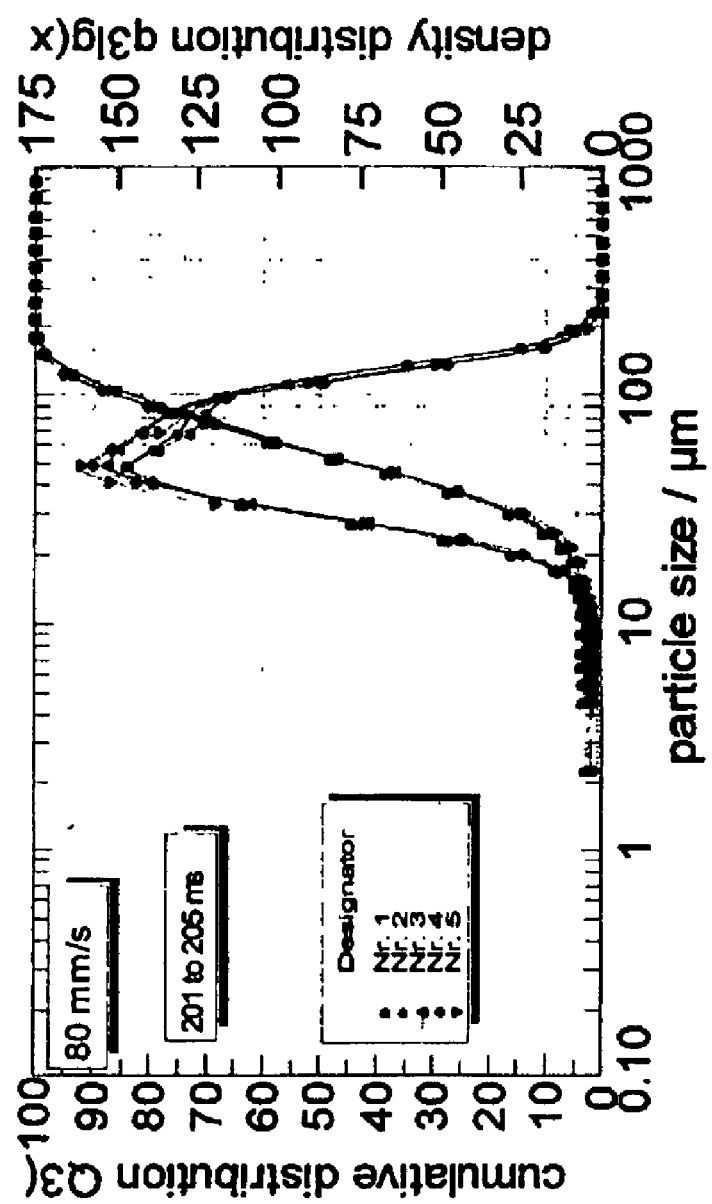

- IM-pFLU-HA liquid
- IN-pFLU-HA liquid
- IN-SFD pFLU-HA + trehalose
- IN-trehalose only FIG. 4 shows a particle size distribution liquid virus particles produced by an accuspray nozzle, as measured by laser diffraction.

Figure 5:
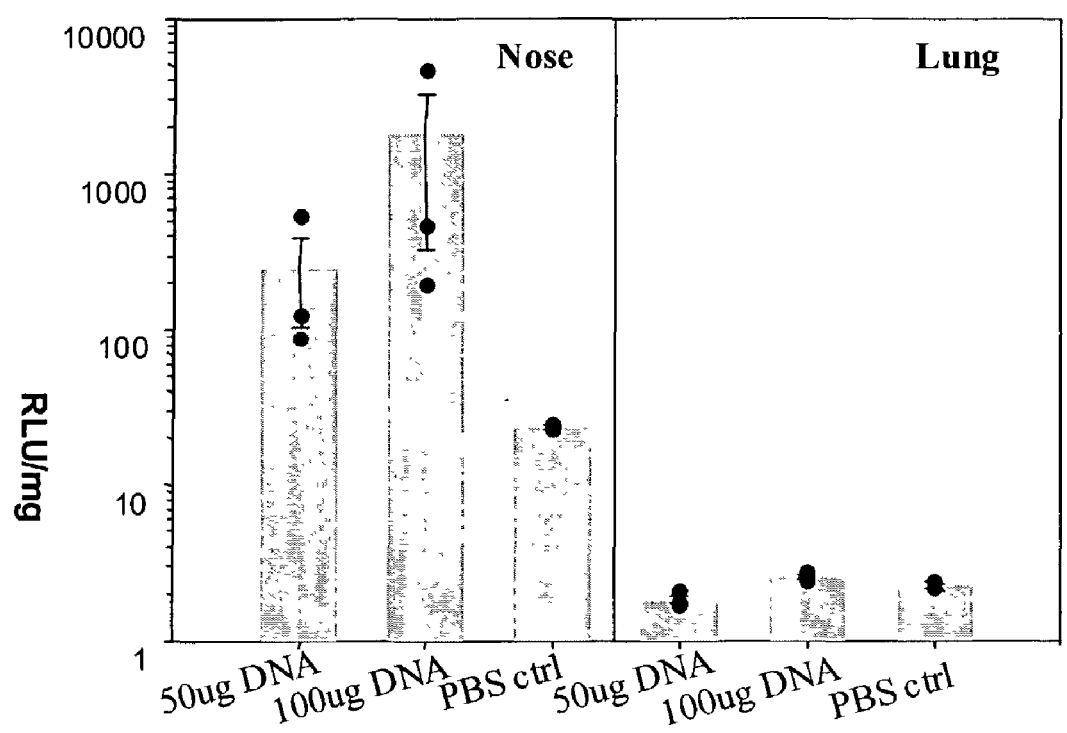

FIG. 5 shows luciferase gene expression after IN liquid pCMV-LUC delivery

Figure 6:
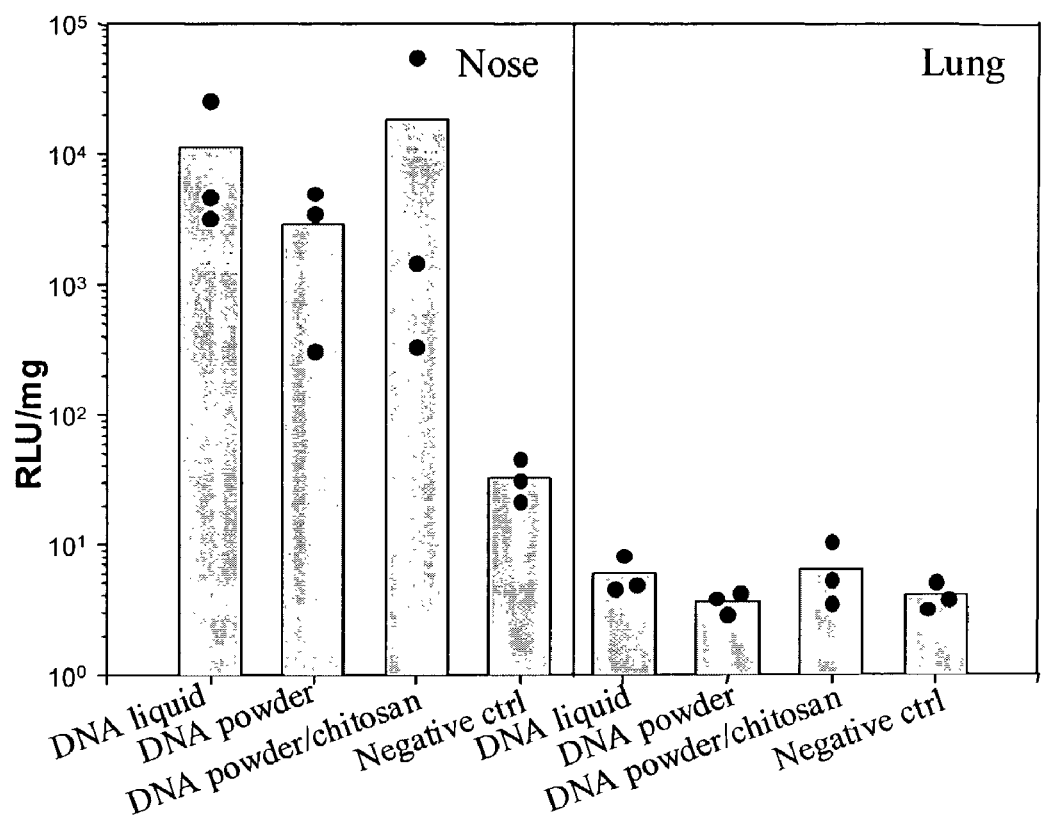

FIG. 6 shows luciferase gene expression in rats after IN pCMV-LUC delivery.

Figure 7:
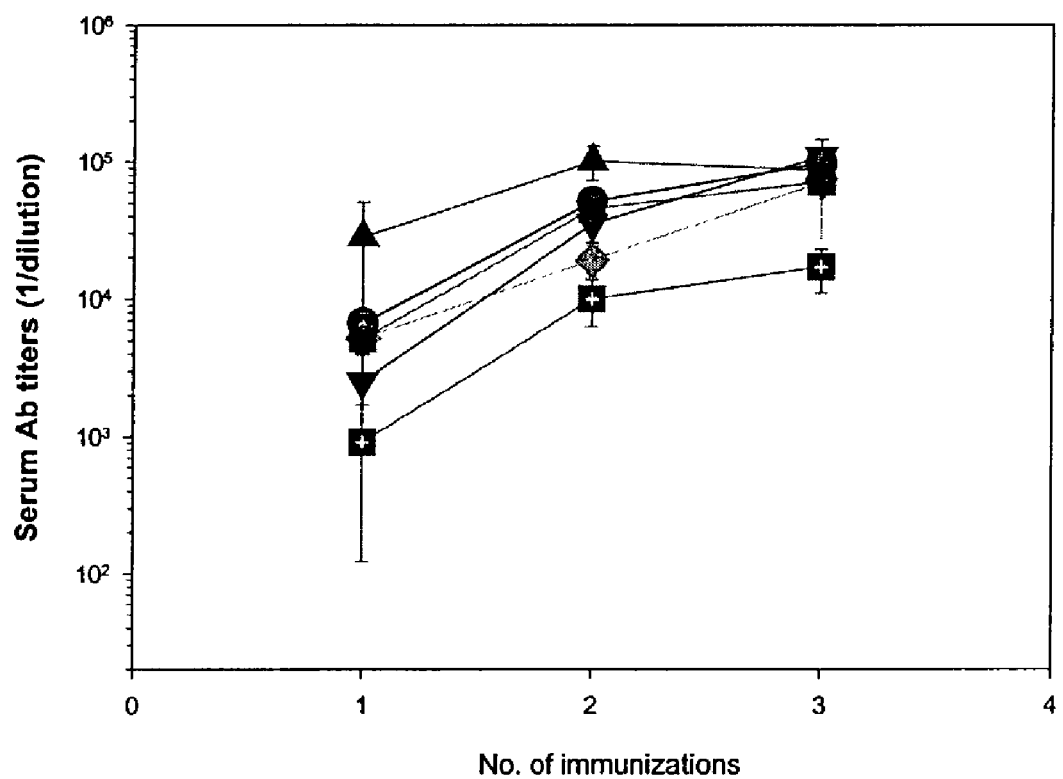

FIG. 7 shows serum Ab titers following pFLU-HA immunization.

Figure 8:
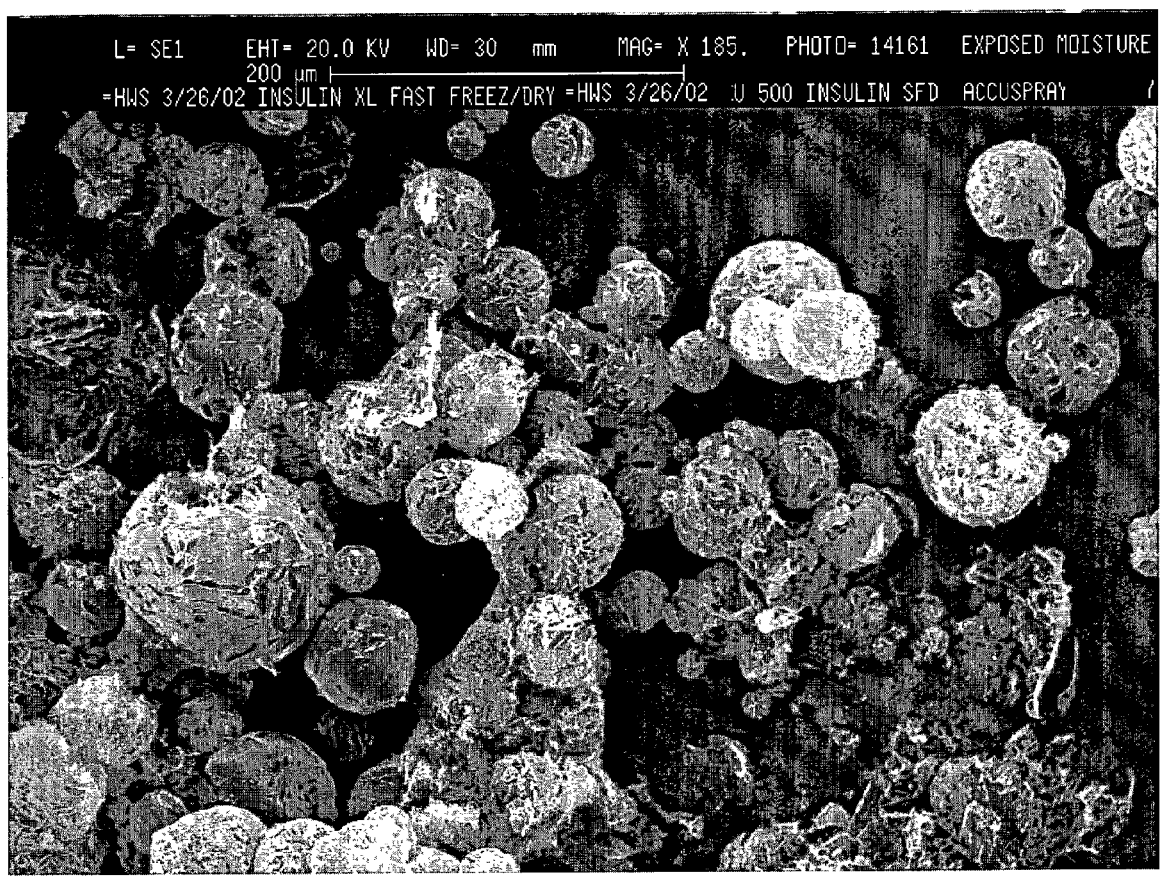

- IM
- IN liquid
- IN FD
- IN FD/chitosan
- IN SFD
- IN SFD/chitosan
- IN negative FIG. 8 shows a scanning electron microscope (SEM) image of SFD insulin sprayed through an accuspray nozzle and dried by lyophilization.

Figure 9:
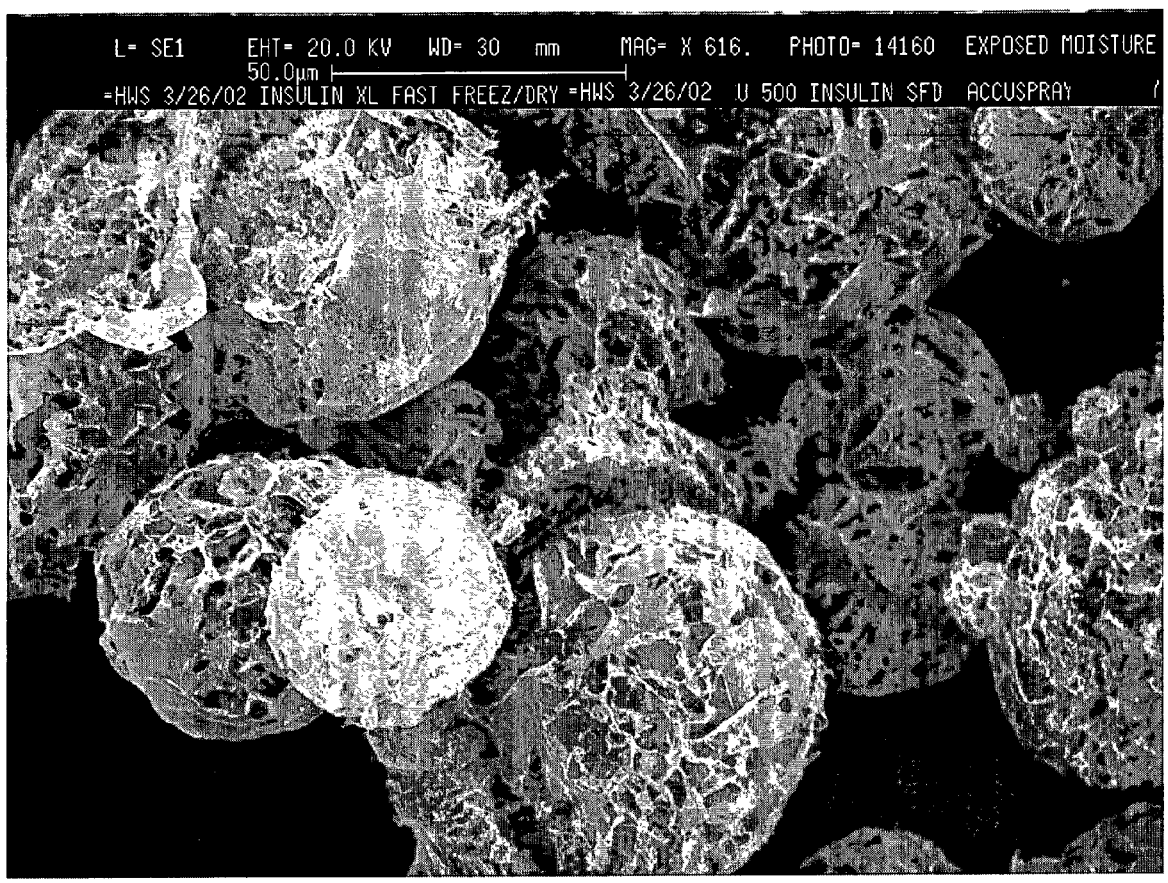

FIG. 9 shows a scanning electron microscope (SEM) image of the SFD insulin shown in FIG. 9, but at a higher magnification.

Figure 10:
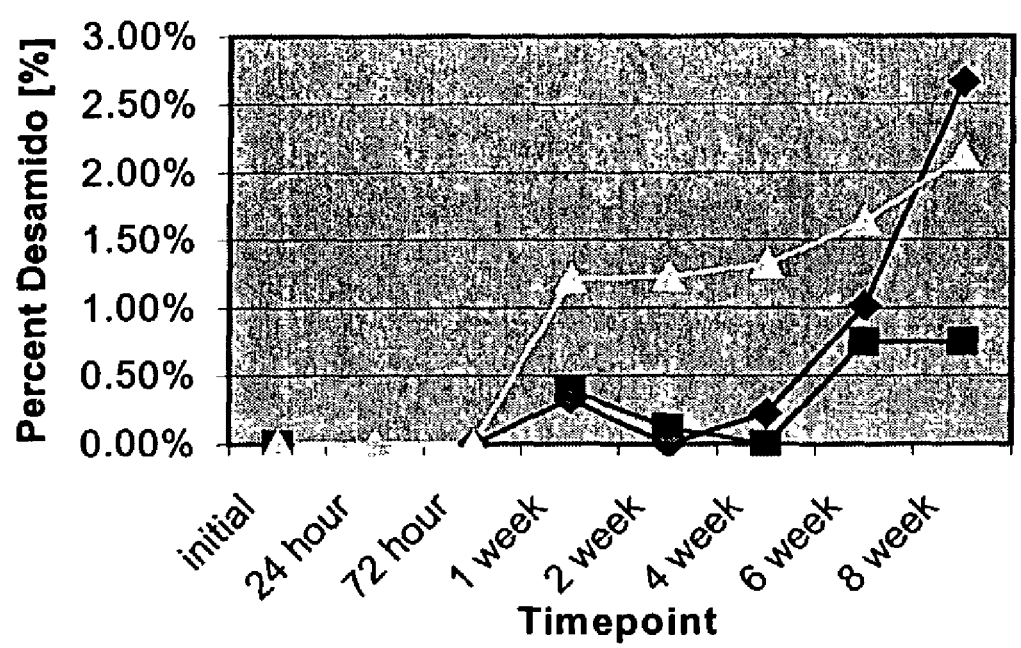

FIG. 10 shows desamido (chemical degradation) detected for SFD and liquid insulin samples, as a measurement of stability.

Figure 11:
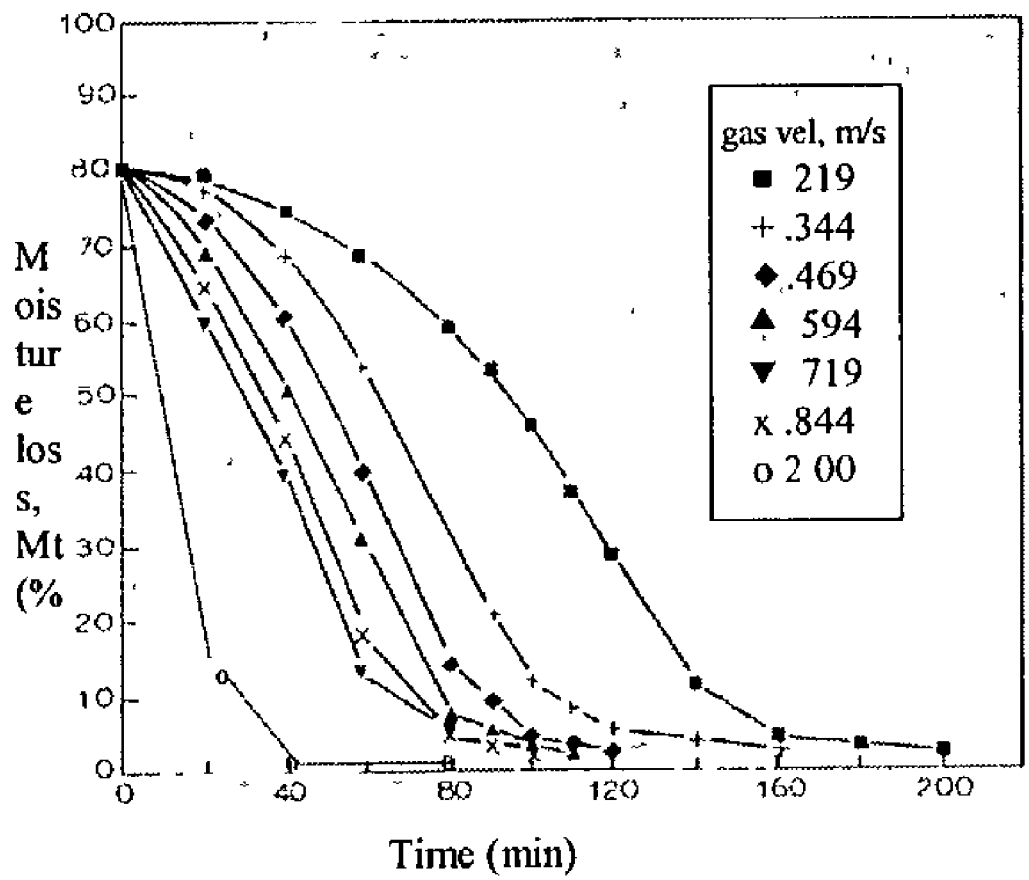

FIG. 11 shows the moisture and drying time of a composition produced by a freeze dry atmosphere method.

Figure 12:
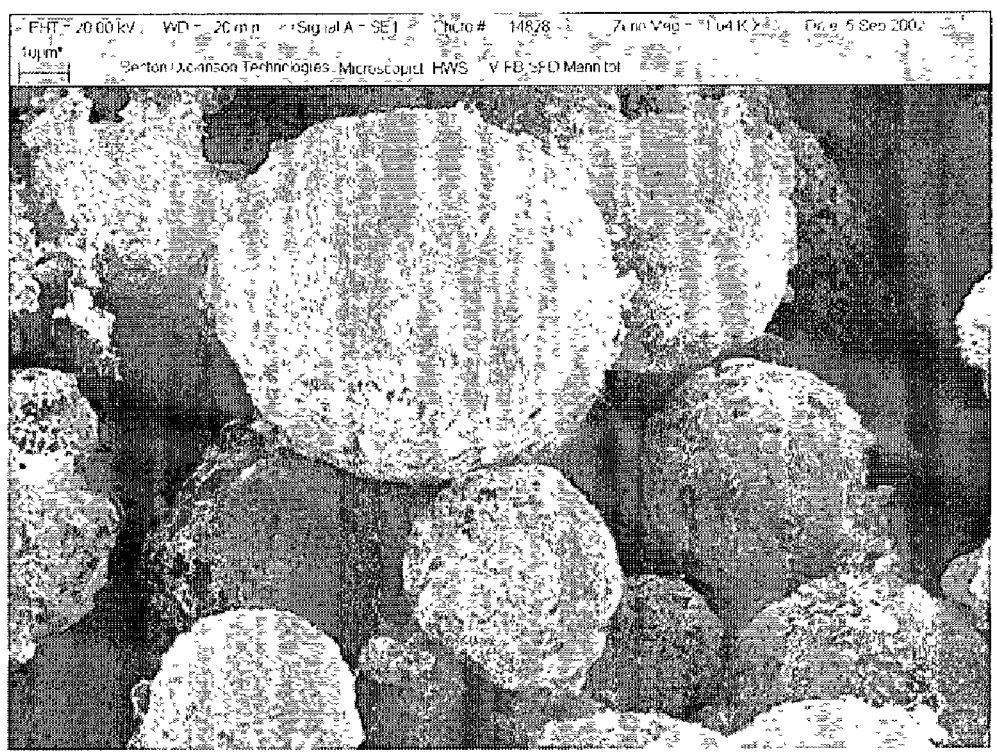

FIG. 12 shows an SEM image of mannitol powders produced by the spray-freeze-atmospheric drying process.

Figure 13A:
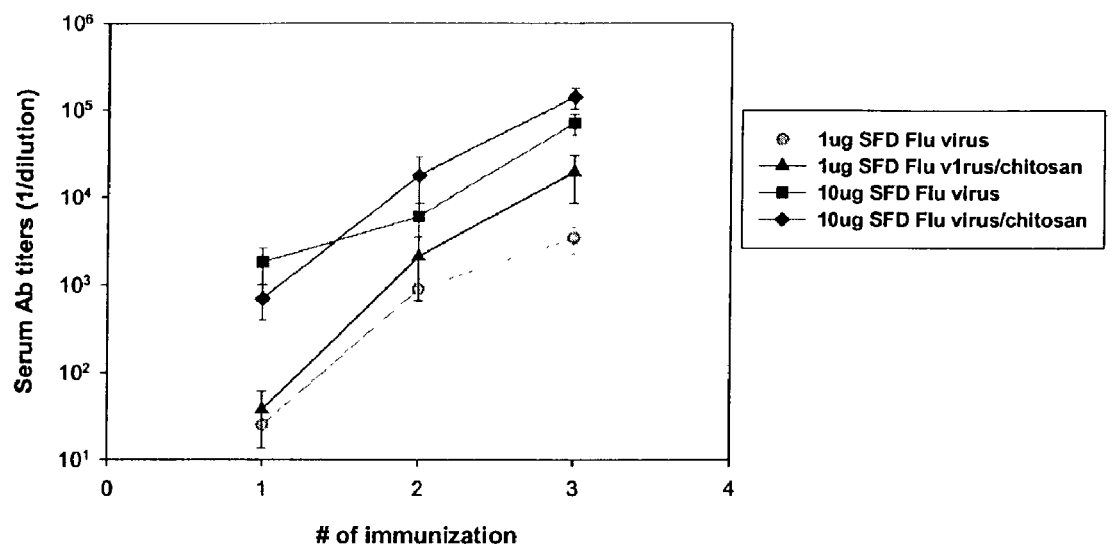

FIG. 13A shows a comparison of serum immune responses following IN delivery of SFD flu vaccine with and without chitosan.

Figure 13B:
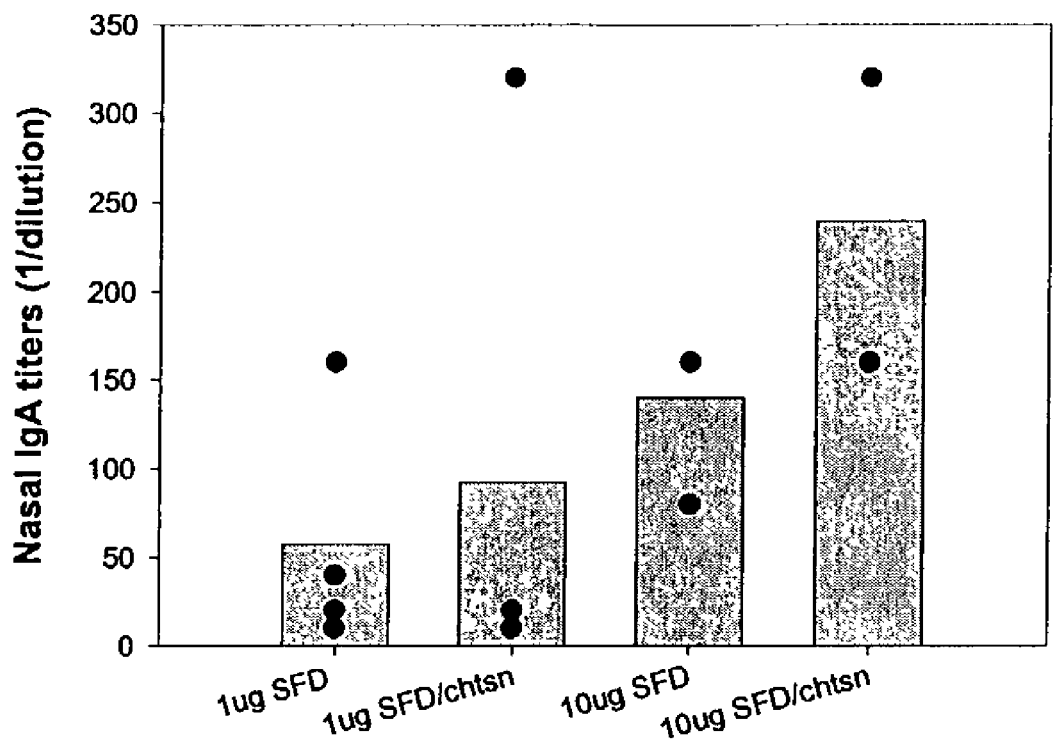

FIG. 13B shows a comparison of nasal mucosal immune responses following IN delivery of SFD flu vaccine with and without chitosan, on day 56.

Figure 14:
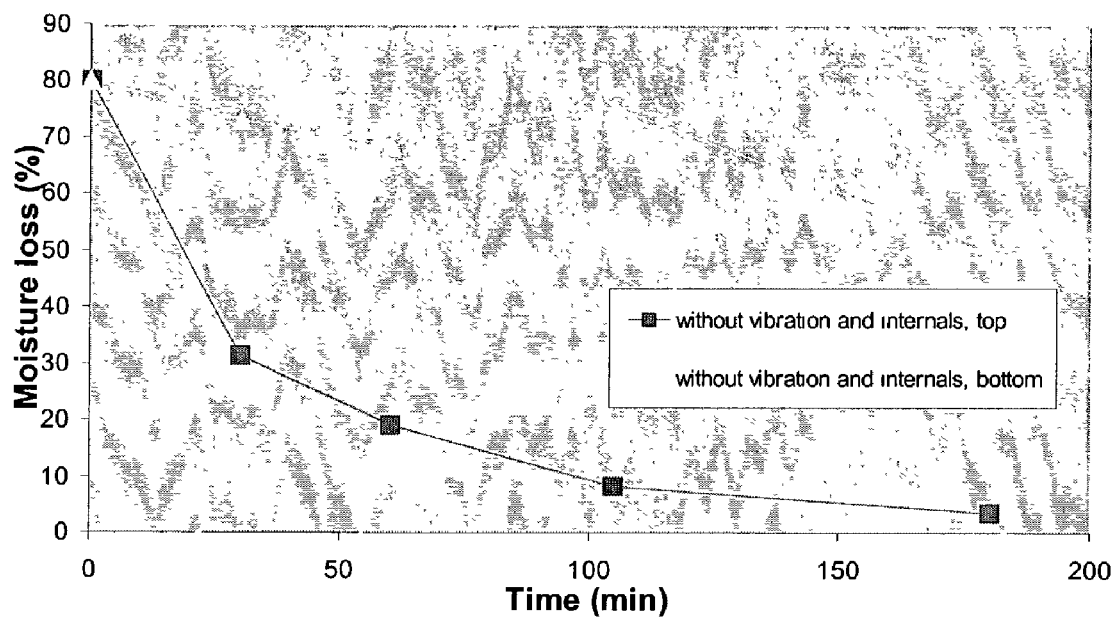

FIG. 14 shows the moisture levels of samples collected from the top and bottom of a fluidized bed, from an integrated SFD process without vibration and internals (low drying gas velocity (0.39 m/s).

Figure 15:
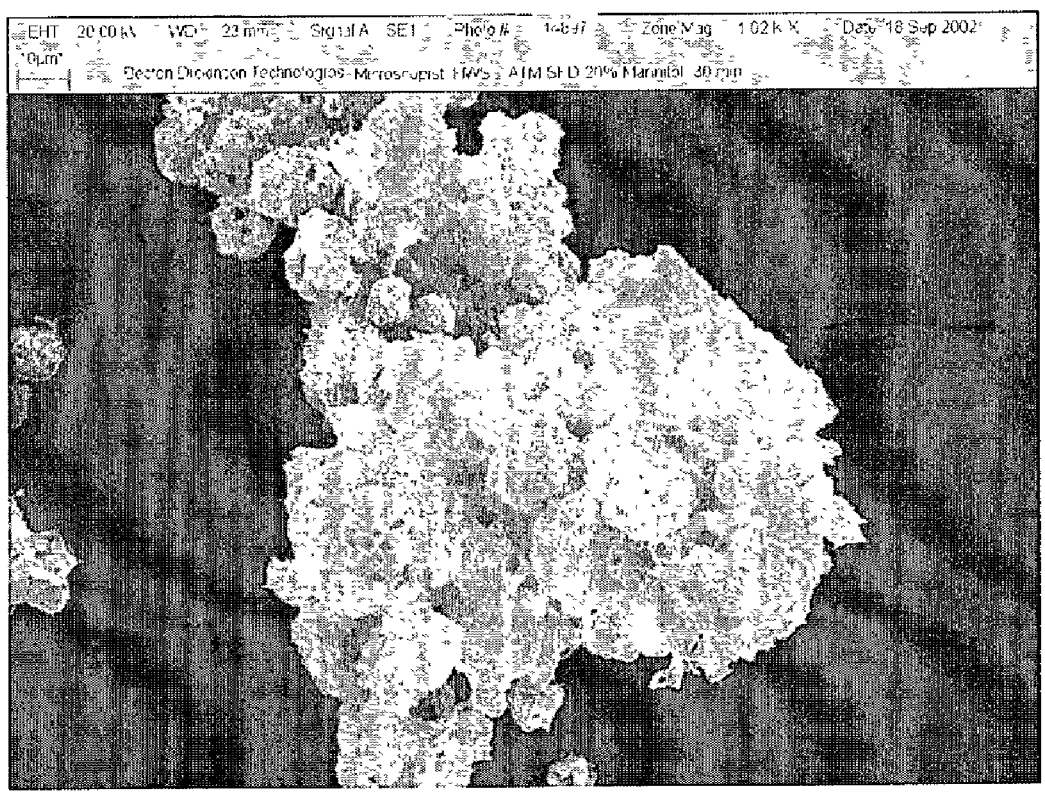

FIG. 15 shows an SEM of particles sampled at 30 minutes from the top of a fluidized bed.

Figure 16:
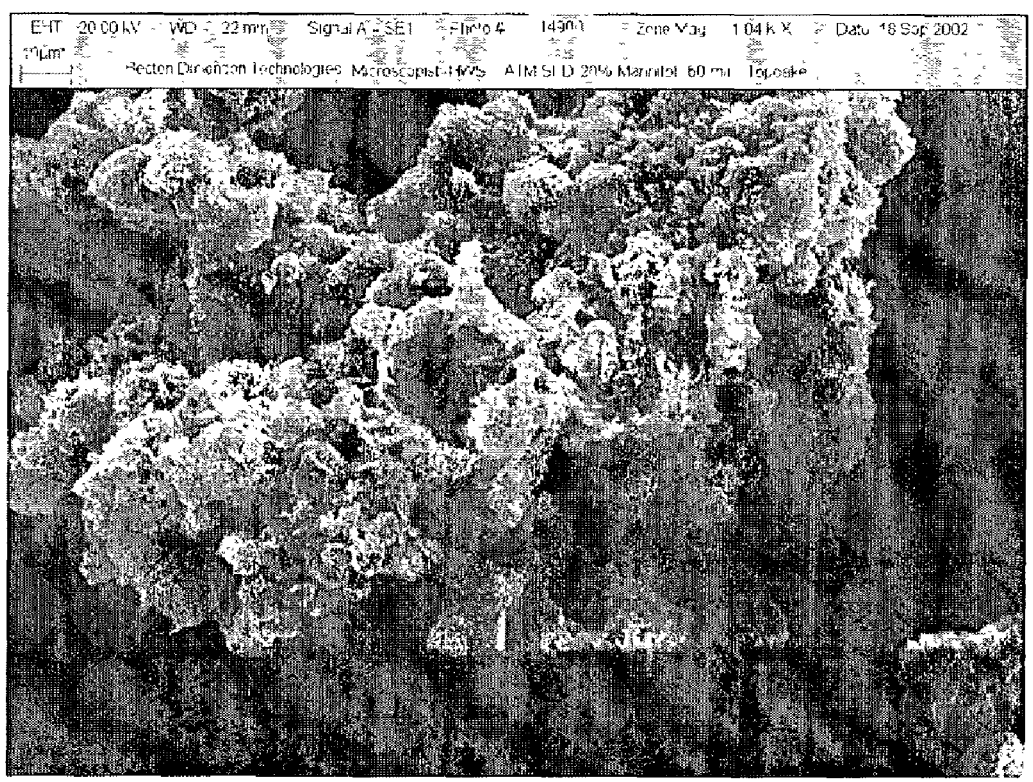

FIG. 16 shows an SEM of particles sampled at 60 minutes from the top of a fluidized bed.

Figure 17:
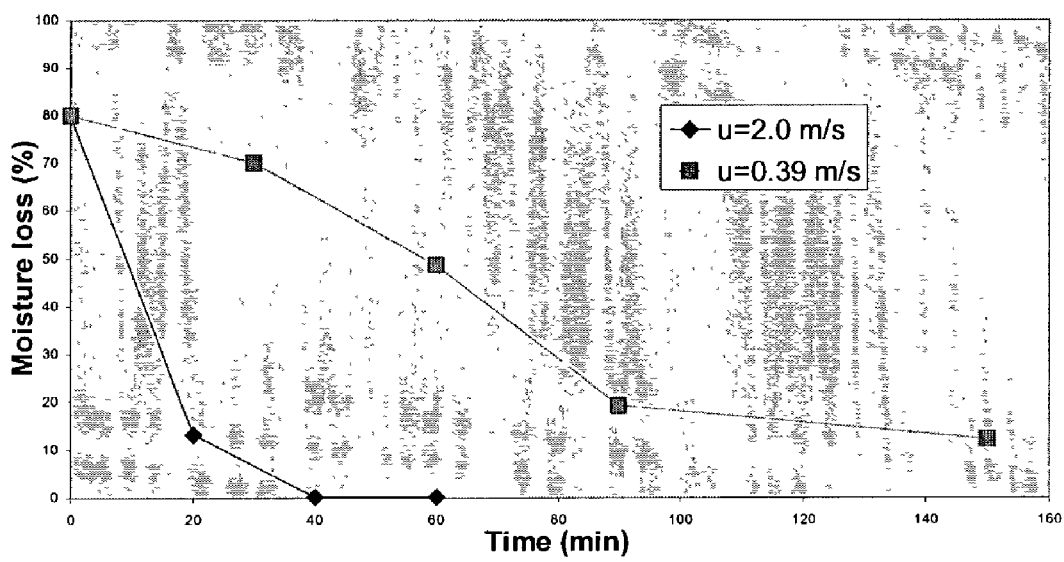

FIG. 17 shows the porosity of powders dried at two different gas velocities. Shown is the effect of flow-rate on sublimination time (V-FB-SFD)

Figure 18:
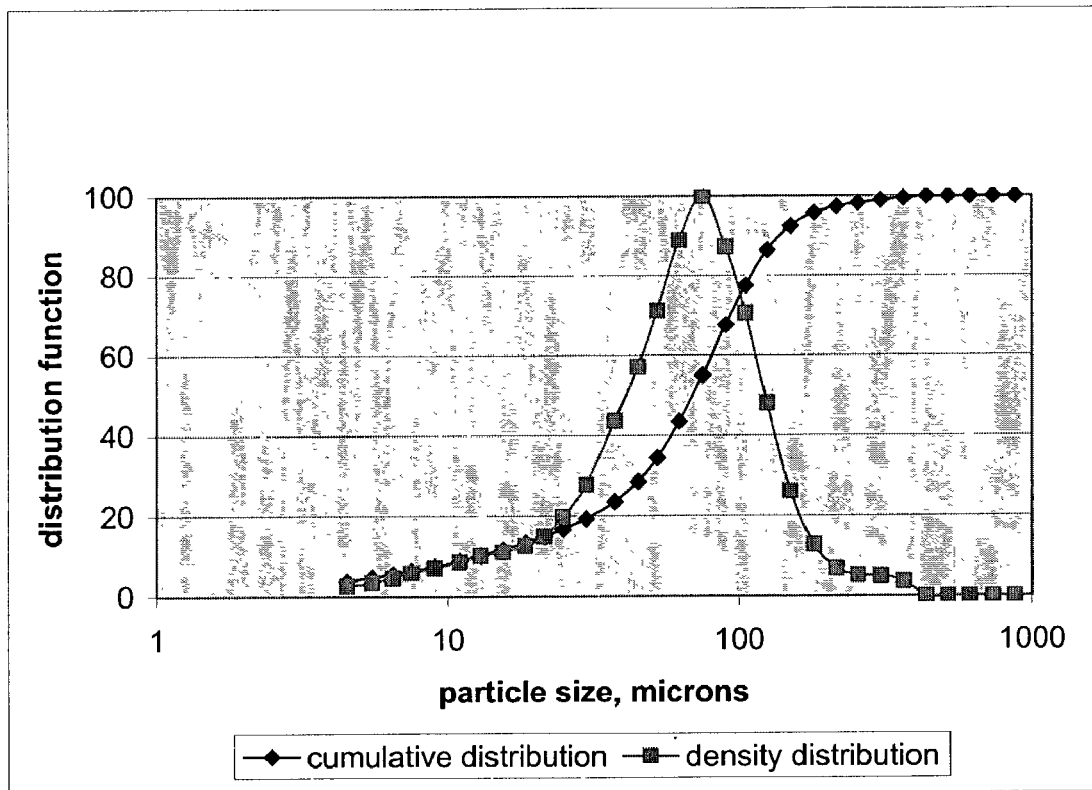

FIG. 18 shows particle size distribution for mannitol particles obtained by spray-freezing through an Accuspray nozzle and drying by lyophilization. The particle size distribution was measured by laser diffraction.

Figure 19:
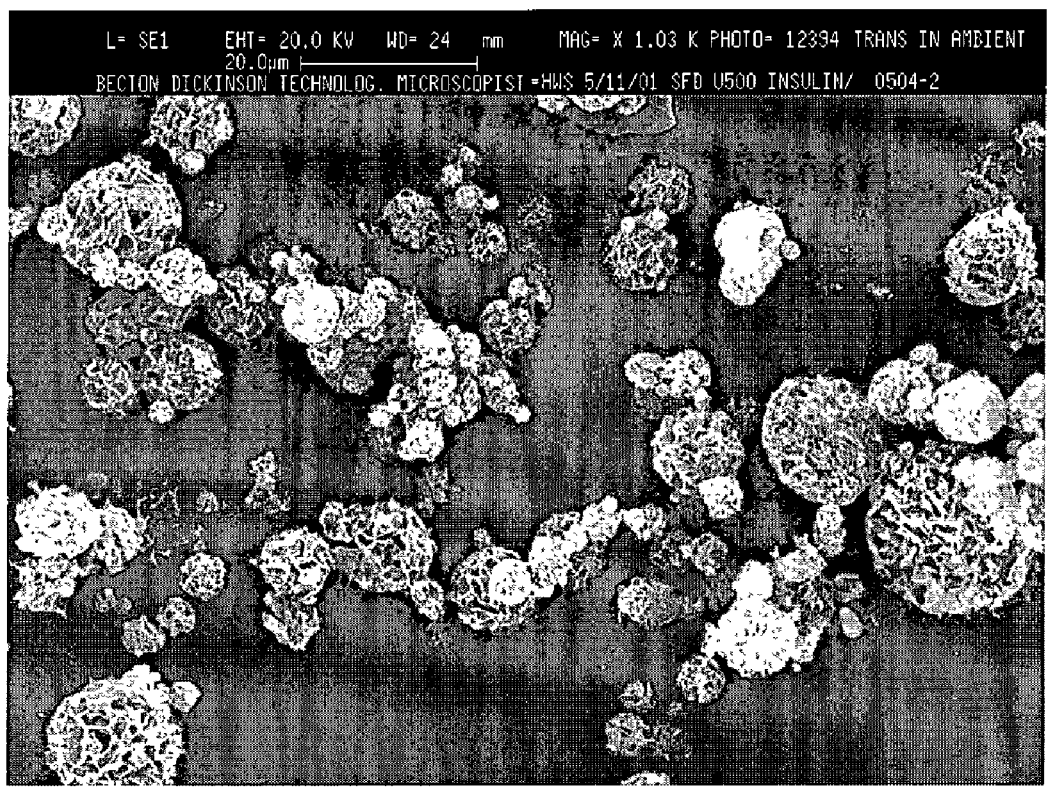

FIG. 19 shows a scanning electron microscope (SEM) image of SFD neat insulin powders (which are more resistant to moisture than insulin/lactose).

Figure 20:
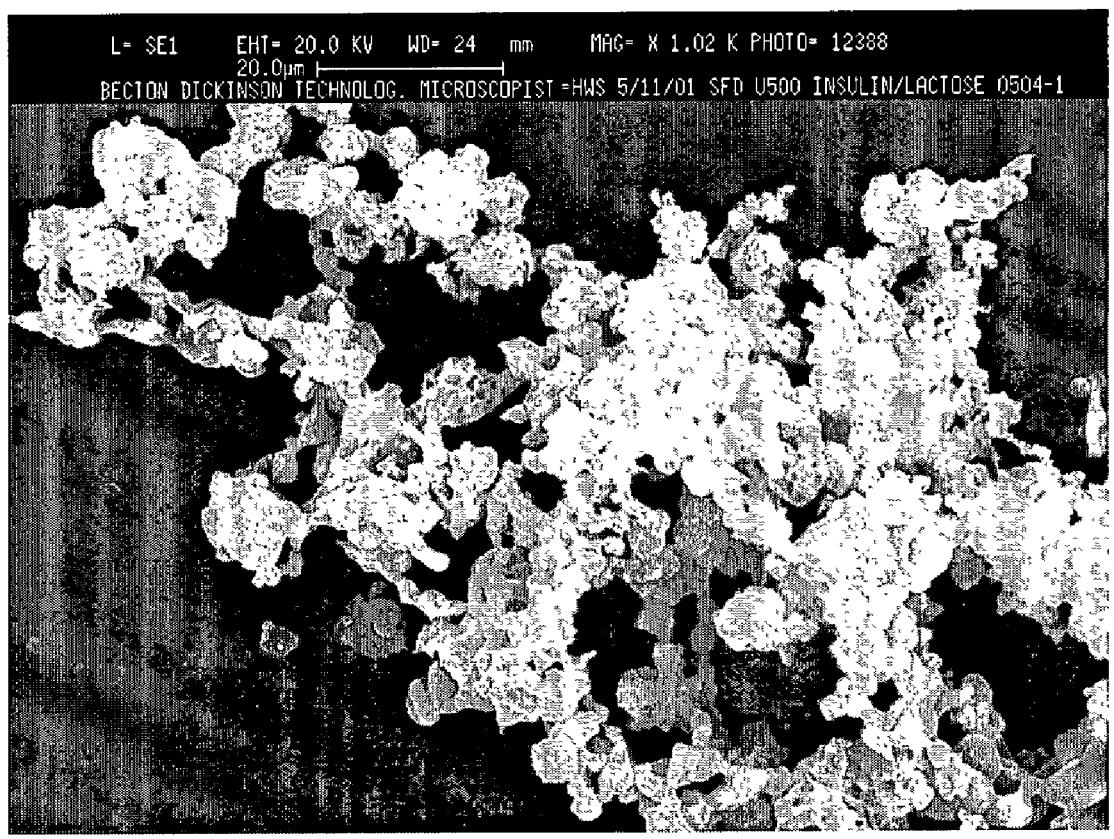

FIG. 20 shows an SEM of SFD insulin/lactose composite powder after exposure to ambient moisture.

Figure 21:
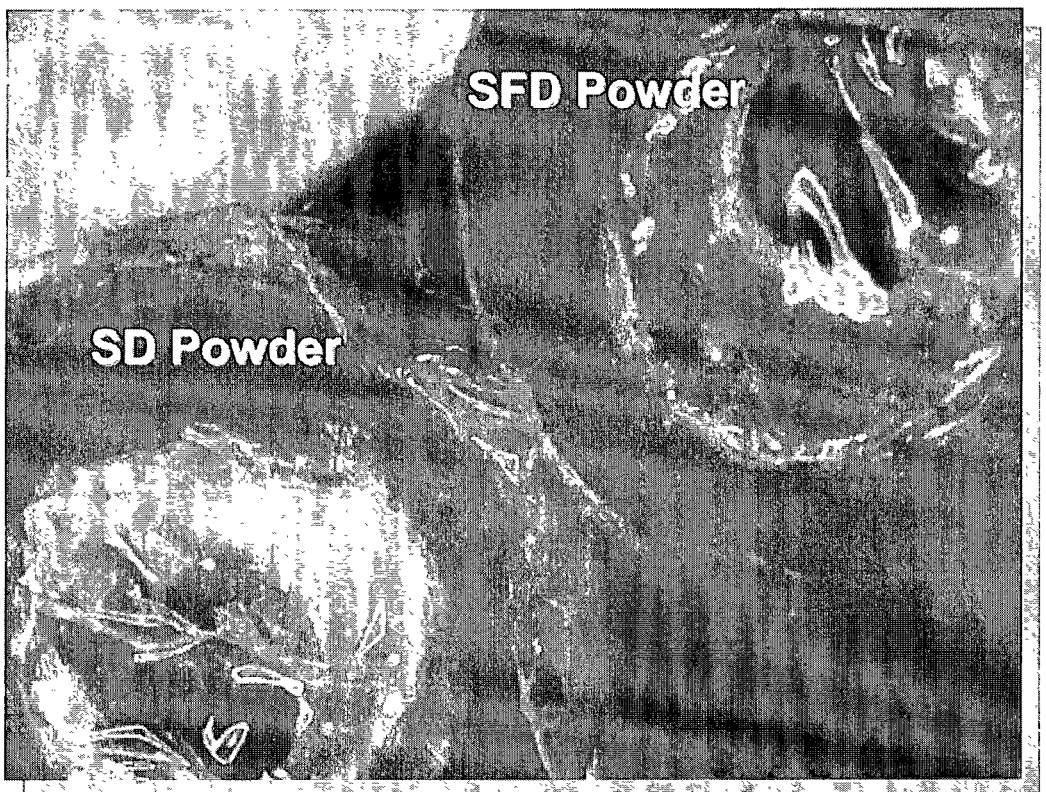

FIG. 21 shows capsules with SD (spray-dry) and SFD (spray-freeze-dry) powders after rupturing the capsule membranes. There is no visible lactose remaining in the capsule with the SFD powder.

DESCRIPTION OF THE INVENTION

The present invention relates, e.g., to methods of preparing dried pharmaceutical compositions, in particulate form (e.g., in a powder); to compositions made by these methods; and to methods of using the compositions to treat patients.

One aspect of the invention is a method of preparing a pharmaceutical composition, comprising one or more of the following steps: atomizing a liquid formulation of a therapeutic or prophylactic agent to produce an atomized formulation; freezing said atomized formulation to form solid particles; and drying said solid particles to produce dried particles (e.g., a powder). Preferably, said atomized formulation comprises droplets having a volume mean diameter (as defined by W. H. Finley, "The mechanics of inhaled pharmaceutical aerosols, an introduction", Academic Press, London, UK (2001)) of between about 35 µm and about 300 µm, more preferably between about 50 µm and about 300 µm, and/or said powder comprises dried particles having a volume mean diameter of between about 35 µm and about 300 µm, more preferably between about 50 µm about 300 µm. Most preferably, these droplets or particles have a volume mean diameter of between about 50 µm and about 100 µm. In a preferred embodiment, at least about 50% of the dried particles have a volume diameter within about 80% of the mean; more preferably, at least about 50% of the dried particles have a volume diameter within about 60% of the mean. In a preferred embodiment, the powder comprises dried particles that have a mean aerodynamic diameter (as defined in W. H. Finley, supra) of between about 8 µm and about 140 µm, more preferably between about 8 µm and about 80 µm, still more preferably between about 20 µm and about 70 µm. This method, and compositions made by the method, are sometimes generally referred to herein as a "spray-freeze-dry" method or compositions.

Particles of the above pharmaceutical compositions are of an appropriate size, density and/or morphology to facilitate intranasal administration. Without wishing to be bound by any particular theory, it is proposed that, following intranasal administration, the compositions described above are delivered to mucous membranes, e.g., of the nasal lining or the sinuses, where they adhere, rather than being propelled through the sinus cavities into the pulmonary system, and that adherence to such mucous membranes allows a faster rate of absorption than with other formulations of therapeutic and prophylactic compositions. When the inventive composition is a vaccine, the time required to mount an effective antibody response is thus reduced, and mucosal immunity (e.g., mediated by an IgA response) is enhanced. Intranasal administration of such inventive vaccines elicits both systemic and nasomucosal IgA immune responses.

Another aspect of the invention is a method prepare a pharmaceutical composition, comprising one or more of the following steps: atomizing a liquid formulation of a therapeutic or prophylactic agent to produce an atomized formulation; freezing said atomized formulation to form solid particles; and drying said solid particles at about atmospheric pressure, in the presence of vibration, internals, mechanical stirring, or a combination thereof, to produce dried particles (e.g. . . . to produce a powder). By "about atmospheric pressure" is meant herein a pressure ranging from about one half atmosphere to about five atmospheres. By "drying" is meant herein removal of the volatile components of the formulation from the solid frozen particles. Preferably, the powder comprises dried particles having a volume mean diameter of between about 35 µm and about 300 µm, more preferably between about 50 µm and about 300 µm, or most preferably between about 50 µm and about 100 µm; and/or the dried particles have a volume mean aerodynamic diameter of between about 8 µm and about 140 µm, preferably between about 8 µm and about 80 µm, more preferably between about 20 µm and about 70 µm. In a preferred embodiment, at least about 50% of the dried particles have a volume diameter within about 80% of the mean; more preferably, at least about 50% of the dried particles have a volume diameter within about 60% of the mean. Preferably, the frozen, solid particles are in a fluidized state as they are being dried. This method, and compositions made by the method, are sometimes referred to herein as "spray-freeze-atmospheric-dry" method or compositions. An advantage of compositions produced by this method is that they do not agglomerate.

Other advantages of the compositions of the invention are that the compositions are readily aerosolized, offer good stability, sterility, emitted dose and preservation of bioactivity, leave little residue in a delivery device such as an inhalation device, and are readily reconstituted in liquid. The particles may exhibit a low tap density, which facilitates the aerosolization of the particles, e.g., for respiratory delivery. The particles exhibit low levels of fines, which renders them easy to handle. The methods of the invention allow for a well-controlled distribution of particle sizes. Therefore, the inventive compositions comprise a well-controlled distribution of particle sizes. The morphology of the particles reduces the potential for their agglomerization and further facilitates aerosolization. The compositions are stable in the absence of refrigeration, allowing for more convenient and less expensive storage and transportation than, e.g., liquid formulations. Compositions of the invention are particularly well suited for mass vaccinations. In one embodiment of the invention, inventive compositions are administered by respiratory (e.g., intranasal) administration. Compositions of the invention are particularly well suited to intranasal administration, since the well controlled particle size distribution allows accurate targeting of the nasal mucosa. Advantages of respiratory administration compared to administration by injection (e.g., intradermal or sub-dermal) include increased patient compliance and enhanced immune responses. Respiratory administration is also advantageous in that it is a non-invasive procedure, which is painless and easy to perform.

The property of tap density is well known to those of skill in the art. Each particle of a solid material has the same true density after grinding, milling or processing, but the material occupies more geometric space. In other words, the geometric density is less, approaching 50% less, than the true density if the particles are spherical.

Handling or vibration of powdered material causes the smaller particles to work their way into the spaces between the larger particles. The geometric space occupied by the powder decreases and its density increases. Ultimately no further natural particle packing can be measured without the addition of pressure. Maximum particle packing is achieved.

Under controlled conditions of tap rate, tap force (fall) and cylinder diameter, the—condition of maximum packing efficiency is highly reproducible. This tap density measurement is formalized in the British Pharmacopoeia method for Apparent Volume, ISO 787/11 and ASTM standard test methods B527, D1464 and D4781 for tap density.

Another aspect of the invention is method of making a pharmaceutical composition as above, wherein the freezing is performed by introducing the atomized formulation into a cold fluid or medium having a temperature below the freezing point of the liquid formulation (the term "a fluid" as used herein encompasses both a gas, such as a compressed gas, and a liquid); wherein said fluid or medium has a boiling point or sublimation point lower than that of the atomized formulation; wherein the drying is performed at about atmospheric pressure (preferably in the presence of vibration, internals, mechanical stirring, or a combination thereof), by lyophilization, or by a combination thereof, preferably wherein the freezing and drying are both performed in a cold gas at about atmospheric pressure (preferably in the presence of vibration, internals, mechanical stirring, or a combination thereof); wherein the therapeutic or prophylactic agent is a protein (e.g., insulin), a nucleic acid or a virus particle, or wherein the therapeutic agent is an immunogenic agent, such as an influenza vaccine, e.g., a vaccine that comprises inactivated influenza particles, a subunit influenza vaccine, or a nucleic acid encoding an influenza haemagglutinin protein, particularly wherein the haemagglutinin protein is under the control of a constitutive promoter, particularly a strong constitutive promoter such as a CMV promoter; wherein the liquid formulation further comprises a pharmaceutically acceptable excipient, such as a mucoadhesive, e.g., chitosan, dermatan sulfate, chondroitin or pectin, or wherein the liquid formulation consists essentially of the therapeutic agent and water.

Another aspect of the invention is a pharmaceutical composition prepared by a method as above; or a pharmaceutical composition that comprises dried particles having a volume mean diameter of between about 35 μm and about 300 μm, preferably between about 50 μm and about 300 μm, more preferably between about 50 μm and about 100 μm and/or wherein the dried particles have mean aerodynamic diameter of between about 8 μm and about 140 μm, more preferably between about 8 μm and about 80 μm, still more preferably between about 20 μm and about 70 μm Preferably, at least about 50% of the dried particles in the composition have a volume diameter within about 80% of the mean; more preferably, at least about 50% of the dried particles have a volume diameter within about 60% of the mean.

Another aspect of the invention is a method of treating a patient in need thereof, comprising administering to the patient an effective amount of a pharmaceutical composition produced by a method of the invention and/or a pharmaceutical composition having the properties noted in the preceding paragraph; wherein the composition is administered by a respiratory, intranasal, intrarectal, intravaginal, sublingual or parenteral route, preferably intranasally, and/or wherein the composition is administered to a mucosal membrane. Another aspect is a method of reducing the amount of a therapeutic or prophylactic agent that is required to produce an efficacious result following intranasal administration to a patient in need thereof, comprising administering to the patient, intranasally, an effective amount of a pharmaceutical composition of the invention. Another aspect is a method of eliciting an immune response in a patient, comprising administering to the patient an effective amount of an immunogenic composition of the invention, e.g., wherein the composition is administered intranasally, and/or wherein the composition is an influenza vaccine of the invention.

Another aspect is a method of preparing a pharmaceutical composition, comprising drying at about atmospheric pressure, in the presence of vibration, internals, mechanical stirring or a combination thereof, solid particles which have been formed by freezing an atomized formulation of a liquid formulation of a therapeutic or prophylactic agent.

Another aspect is a method of preparing a pharmaceutical composition, comprising atomizing a liquid formulation of said therapeutic or prophylactic agent to produce an atomized formulation, such that, following freezing of said atomized formulation to form solid particles, and drying of said solid particles to produce a powder, the dried powder comprises dried particles having an average mean size diameter of between about 35 μm and about 300 μm, preferably between about 50 μm and about 300 μm, and more preferably between about 50 μm and about 100μ, wherein at least about 50% of said dried particles have a volume diameter within about 80% of the mean, and said dried particles having a mean aerodynamic diameter of between about 8 μm and about 140 μm.

Any of a variety of therapeutic or prophylactic agents can be used in the methods and compositions of the invention. A "therapeutic agent" (sometimes referred to herein as an "active pharmaceutical agent" or API), as used herein, means an agent that can elicit a therapeutic effect in a cell, tissue, organ or patient to which it is administered. Compositions that comprise one or more therapeutic agents can produce a "clinically efficacious result" when administered to a patient. As used herein, the term a "clinically efficacious result" means a clinically useful biological response, and applies both to diagnostic and therapeutic uses. For example, a composition of the invention can be used in a method of diagnostic testing, and/or to treat, prevent and/or ameliorate symptoms of a disease or a condition in a patient.

The therapeutic agents can be any of a variety of types, including, e.g., polypeptides (proteins), polynucleotides (nucleic acids), small molecules such as steroids and viral particles. The terms polypeptide and protein are used interchangeably herein, as are the terms polynucleotide and nucleic acid.

Suitable polypeptides or peptides include, but are not limited to, growth factors, cytokines, antigens, antibodies, interleukins, lymphokines, interferons, enzymes, etc., including, but not limited to, anti-IgE antibodies, tissue plasminogen activator (tPA), calcitonin, erythropoeitin (EPO), factor IX, granulocyte colony stimulating factor (G-CSF), granulocyte macrophage colony stimulating factor (GM-CSF), growth hormone (particularly human growth hormone), heparin (including low molecular weight heparin), insulin, insulin-like growth factors I (IGF-I) and II (IGF-II), interleukins, interferons α, β, and γ, luteinizing hormone releasing hormone, somatostatin and analogs, vasopressin and analogs, follicle stimulating hormone, amylin, ciliary neurotrophic factor, growth hormone releasing factor, insulinotropin, macrophage colony stimulating factor(M-CSF), nerve growth factor, parathryoidhormone, α-1 antitrypsin, anti-RSV antibody, DNase, Her2, CFTR (cystic fibrosis transmembrane conductance regulator gene product, useful to treat cystic fibrosis), insulin, etc. In a preferred embodiment, the polypeptide is insulin. Polypeptides such as marker proteins can also be used.

In a preferred embodiment, the polypeptides are found within or on the surface of infectious agents, such as bacteria, viruses, protozoan or other parasites, including malaria, or the like. Such polypeptides can serve as immunogenic agents, for use, e.g., in a vaccine.

The polypeptide can be a naturally occurring one or it can be produced recombinantly. It can be modified by any of a variety of art-recognized modifications, such as in the variant polypeptides discussed in US2002/0052475. Polypeptides used in the invention can be fragments of full-length proteins. Any desirable size (length) polypeptide can be used. For example, a peptide that comprises one or more epitopes and/or antigenic sequences can serve as an agent to elicit an immune response.

Suitable polynucleotides include, e.g., vectors comprising recombinant sequences that encode therapeutic polypeptides of interest. These polynucleotides can any encode any of the therapeutic polypeptides noted above, or others. Methods to clone such sequences and to generate recombinant vectors in which the sequences of interest are operatively linked to suitable expression control sequences, are routine and conventional. Typical methods include those described in, among many other sources, Sambrook, J. et al. (1989) *Molecular Cloning, a Laboratory Manual*, Cold Spring Harbor Press, Cold Spring Harbor, N.Y., and Ausubel, F. M. et al. (1995). *Current Protocols in Molecular Biology*, NY, John Wiley & Sons. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Suitable expression control sequences, such as strong constitutive or regulatable promoters, will be evident to the skilled worker.

The polynucleotide can be a naturally occurring one or it can be produced recombinantly. Polynucleotides used in the invention can be fragments of full-length nucleic acids, e.g., fragments that encode fragments of full-length proteins. Any desirable size polynucleotide can be used, provided that it provides a clinically efficacious result.

Polynucleotides which can be used in compositions and methods of the invention can take any of a variety of forms that will be evident to the skilled worker, including DNA, RNA, PNA, LNA, oligonucleotides, single or double strand molecules, etc. The nucleic acids can comprise any of a number of known modifications that can aid, e.g., in stabilizing them or enhancing uptake into cells. Such modifications include, e.g., those discussed in U.S. Pat. No. 6,455,292.

In a preferred embodiment, the polynucleotide serves as a vaccine, e.g., a DNA vaccine. The construction and use of one such DNA vaccine, which encodes the influenza haemagglutinin protein and which provides protection against at least some symptoms of influenza infection, is discussed in more detail elsewhere herein. See, e.g., Examples 5-8. Such nucleic acids may encode full-length proteins or fragments thereof, e.g., antigenic peptides that can elicit an immune response.

The nucleic acids can comprise coding or non-coding (e.g., regulatory) sequences. In addition to encoding polypeptides, the nucleic acids can be, e.g., antisense molecules or ribozymes. For a discussion of some of the well-known types of antisense molecules or ribozymes, see, e.g., U.S. Pat. No. 6,455,292.

Suitable virus particles include, e.g., partially or fully inactivated viral particles that can serve as antigens for vaccines, such as, e.g., influenza, RSV and polioviruses. In a preferred embodiment, the virus is inactivated influenza virus. Typical strains of influenza include, e.g., A/PR/8/34 and the Port Chalmers strain. Subunit vaccines, prepared by conventional methods, are also included. In another embodiment, conventional viral vectors that are suitable for intranasal administration, including but not limited to adenovirus-based vectors or AAV-based vectors, comprising one or more genes that encode therapeutic proteins, are included. Any suitable therapeutic gene can be used, including, e.g., genes suitable for treatment of cystic fibrosis.

Suitable steroids include, e.g., conventional steroids for treating asthma, bronchial spasms, or other conditions, which are well known to those of skill in the art.

A therapeutic agent of interest can be initially formulated as a liquid formulation, using any of a variety of conventional liquids. Preferably, the liquid is an aqueous one, such as, e.g., water (e.g., injectable grade water) or any of a variety of conventional buffers, which may or may not contain salts. The pH of the buffer will generally be chosen to stabilize the protein or other type of therapeutic agent of choice, and will be ascertainable by those in the art. Generally, this will be in the range of physiological pH, although some proteins can be stable at a wider range of pHs, for example acidic pH. Thus, preferred pH ranges of the initial liquid formulation are from about 1 to about 10, with from about 3 to about 8 being particularly preferred, and from about 5 to about 7 being especially preferred. As will be appreciated by those in the art, there are a large number of suitable buffers that may be used. Suitable buffers include, but are not limited to, sodium acetate, sodium citrate, sodium succinate, ammonium bicarbonate and carbonate. Generally, buffers are used at molarities from about 1 mM to about 2 M, with from about 2 mM to about 1 M being preferred, and from about 10 mM to about 0.5 M being especially preferred, and 50 to 200 mM being particularly preferred. Generally, salts, if present in the liquid solution, are used at molarities from about 1 mM to about 2 M, with from about 2 mM to about 1 M being preferred, and from about 10 mM to about 0.5 M being especially preferred, and 50 to 200 mM being particularly preferred. Suitable salts include, but are not limited to, NaCl.

The liquid formulation can be in any of a variety of forms, e.g., a solution, a suspension, a slurry or a colloid.

Optionally, the liquid formulation can comprise one or more conventional pharmaceutically acceptable excipients. "Excipients" generally refer to compounds or materials that are added to enhance the efficacy of a formulation of an API. Examples include, e.g., cryoprotectants and lyoprotectants, which are added to ensure or increase the stability of the protein during the spray-freeze dry process or spray-freeze atmosphere dry process, and afterwards, for long term stability and flowability of the powder product. Suitable protectants are generally relatively free flowing particulate solids, do not thicken or polymerize upon contact with water, are essentially innocuous when inhaled by a patient or otherwise introduced into a patient, and do not significantly interact with the therapeutic agent in a manner that alters its biological activity. Suitable excipients include, but are not limited to, proteins such as human and bovine serum albumin, gelatin, immunoglobulins, carbohydrates including monosaccharides (galactose, D-mannose, sorbose, etc.), disaccharides (lactose, trehalose, sucrose, etc.), cyclodextrins, and polysaccharides (raffinose, maltodextrins, dextrans, etc.); an amino acid such as monosodium glutamate, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; surfactants; and combinations thereof. Preferred excipients include e.g., trehalose, sucrose and mannitol. Another class of excipient, mucoadhesives, are often used to increase contact of an API with mucosal surfaces. Examples of mucoadhesives include, e.g., chitosan, dermatan sulfate, chondroitin, and pectin. Additionally, conventional cosolvents, which improve the solubility of APIs, can be added to liquid formulations suitable for the SFD processes disclosed herein.

Generally, when mucoadhesives are used, they are used in amounts ranging from about 1 to 95 wt %, with from about 1 to 50 wt % preferred, from about 5 to 50 wt % being especially preferred, and from about 5 to 20% being particularly preferred. In general, cryoprotectants are used at a concentration of between about 5 wt % and about 95 wt %.

In one embodiment, the dried powders of the invention are later combined with bulking agents or carriers, which are used to reduce the concentration of the therapeutic agent in the powder being delivered to a patient; that is, it may be desirable to have larger volumes of material per unit dose. Bulking agents may also be used to improve the dispersibility of the powder within a dispersion device, and/or to improve the handling characteristics of the powder. This is distinguishable from the use of bulking agents or carriers during the spray-drying process. Suitable bulking agents are generally crystalline (to avoid water absorption) and include, but are not limited to, lactose and mannitol. Accordingly, bulking agents such as lactose, if added, may be added in varying ratios, with from about 99:1 of a therapeutic agent of interest to bulking agent to about 1:99 being preferred, and from about 1:5 to about 5:1 being more preferred, and from about 1:10 to about 1:20 being especially preferred.

Liquid formulations of the invention can be atomized by any of a variety of conventional procedures. For example, the liquid can be sprayed through a two-fluid nozzle, a pressure nozzle, or a spinning disc, or atomized with an ultrasonic nebulizer or a vibrating orifice aerosol generator (VOAG). In one embodiment, a liquid formulation is atomized with a pressure nozzle such as a BD AccuSpray nozzle.

In a preferred embodiment, atomization conditions are optimized such that the mean mass diameter of the atomized droplets (e.g., nebulized droplets) is at least about 20µ, preferably between about 35 µm and about 300 µm, more preferably between about 50 µm and about 300 µm, still more preferably between about 50 µm and about 100 µm. Methods to optimize the generation of droplets of the desired size are conventional. Among the conditions that can be varied are atomization gas flow, atomization gas pressure, liquid flow rate, etc. Also, the type and size of the nozzle can be varied. Liquid drop size can be readily measured, using conventional techniques, such as laser diffraction. The size of dried particles can be measured by conventional techniques, such as, e.g., scanning electron microscopy (SEM) or laser diffraction. FIGS. 4 and 18, e.g., show typical particle size distribution of a liquid sample and a dry powder sample, respectively, as measured by laser diffraction, for samples produced by a method illustrated in Example 1.

In one embodiment, in which frozen, atomized particles are dried at about atmospheric pressure, as is discussed elsewhere herein, the size of the atomized droplets can be, e.g., at least about 20 µm, preferably between about 20 µm and about 300 µm, more preferably between about 35 µm and about 100 µm or between about 50 µm and about 100 µm Following the atomization of a liquid formulation, the droplets are rapidly frozen to form solid particles. Preferably, the droplets arc frozen immediately, or substantially immediately, after the atomization step.

In one embodiment, the droplets are frozen by immersing them in a cold liquid that is below the freezing point of the liquid formulation from which the atomized droplets were formed. In a preferred embodiment, the temperature of the cold liquid is about −200° C. to −80° C., more preferably between about −200° C. to −100° C., most preferably about −200° C. (liquid nitrogen is about −196° C.). Any suitable cold liquid may be used, including liquid nitrogen, argon and hydrofluoroethers, or a compressed liquid, such as compressed fluid $CO_2$, helium, propane or ethane, or equivalent inert liquids, as is well known in the art. For example, in one embodiment, a liquid preparation of a therapeutic agent is atomized through a spray nozzle that is positioned above a vessel containing a suitable cold liquid, such as, e.g., liquid nitrogen. The droplets freeze instantaneously upon contact with the cold liquid. Example 2 shows the preparation of a composition of inactivated flu virus particles that utilizes such a freezing procedure.

In another embodiment, the droplets are frozen by passage through a gas (e.g., cold air, nitrogen, helium or argon), in a cooling chamber, wherein the gas is below the freezing point of the droplets. In a preferred embodiment, the cold gas is about −5° C. to −60° C., more preferably between about −20° C. to −40° C. The gas can be cooled by conventional methods, such as by cooling coils, heat exchangers or chiller condensers. The temperature of the gas can be reduced with conventional procedures, e.g., with liquid nitrogen, solid carbon dioxide or an equivalent cryogenic agent to produce the subfreezing temperatures. Examples 1a and 1b illustrate typical apparati and methods that can be used to produce compositions of the invention, in which nebulized droplets are cooled in a gas by passage through suitable cooling chambers.

Following the formation of solid frozen particles, the particles are dried to produce a powder. By "dry" is meant having a negligible amount of liquid, e.g., having a moisture content such that the particles are readily dispersible to form an aerosol, e.g. in an inhalation device. This moisture content is generally below about 15% by weight water, with less than about 10% being preferred and less than about 1% to about 5% being particularly preferred.

In one embodiment of the invention, the frozen droplets are dried by lyophilization (freeze-drying, under vacuum), using a conventional lyophilization apparatus. This method is generally called a "spray-freeze-dry" or SFD method, and compositions made by the method are called "spray-freeze-dry" or SFD compositions. For example, in one embodiment, when particles have been frozen by spraying them into a vessel (such as a Virtis freeze-drying flask) containing liquid nitrogen, the vessel can then be attached to a conventional lyophilizer and the excess liquid nitrogen evaporated off. The frozen aerosol is typically dried within about 48 hours and reaches a moisture level below about 1 wt %. Alternatively, droplets that have been frozen in cold air at about atmospheric pressure and, optionally, partially dried at about atmospheric pressure (as is discussed below) can then be placed in a lyophilization flask and subjected to lyophilization.

In another embodiment, the frozen droplets are dried by sublimation in a cold, desiccated gas (e.g., air, nitrogen or helium) stream at about atmospheric pressure. By "about atmospheric pressure" is meant herein a pressure ranging from about one half atmosphere to about five atmospheres. The temperature of the gas can be reduced by any of a variety of conventional procedures, e.g., with liquid nitrogen, solid carbon dioxide or an equivalent cryogenic agent. Particles of the invention that are dried in such a manner are sometimes referred to herein as "spray-freeze-atmosphere-dried" particles. In a preferred embodiment, atomized droplets are frozen and dried in the same "spray-freeze-atmosphere-dry" chamber, allowing the freezing and drying procedures to be carried out in a single step.

One apparatus and method for drying solid, frozen particles in cold air at about atmospheric pressure is disclosed in Leuenberger, U.S. Pat. No. 4,608,764. See also Examples 1a and 1b herein. Other types of conventional apparatus can also be used.

In a preferred embodiment, e.g., as shown in Examples 1b and 11, frozen atomized particles are dried in a cold gas at about atmospheric pressure in the presence of conditions that enhance fluidization of the particles. In a most preferred embodiment, the frozen, atomized particles are dried in the presence of vibration, internals, mechanical stirring, or combinations thereof, during the drying process. The term, "internals," as used herein, refers to any physical barrier inside a chamber (e.g., the SFD chamber) or fluidized bed, such as, e.g., blades, plates or other barriers. Such treatments allow the particles to achieve a fluidized state. A method and apparatus for achieving such fluidization is discussed in Examples 1b and 11.

The method and apparatus described in Examples 1b and 11 also help to prevent channeling. Channeling is one of the most undesirable fluidization characteristics of fine particles and can occur at low or high fluidization velocity. This happens when gas passes up through voids extending from the distributor to the bed surface. These vertical channels may move across the bed with time, resulting in defluidization of the bed. There are also small cracks in the bed, which drain into these vertical channels. With increasing gas velocity, not only small channels but also large channels, also called ratholes, are formed for some extremely cohesive particles. This difficulty arises because the interparticle forces are noticeably greater than the forces the fluid can exert on the particles.

Spray-frozen powder, which is spray-frozen by using, e.g., a two-fluid nozzle, a pressure nozzle or an ultrasonic nozzle, can be very difficult to fluidize. When dried in a fluidized bed, such particles channel or agglomerate easily, making them difficult or even impossible to dry quickly and completely. The present inventors have recognized that the introduction of vibration, internals, mechanical stirring, or a combination thereof, during the drying process, can be effective in allowing such particles to become fluidized.

In another embodiment, the frozen droplets are dried by a combination of sublimation in a cold, desiccated gas (e.g., air) stream at about atmospheric pressure, as described above, and lyophilization. For example, a composition that has been partially dried at about atmospheric pressure (e.g., to form a cake or a powder that still contains undesirable amounts of liquid) is removed to a lyophilizer, in which the composition is dried further.

Conventional methods can be used to collect the dried compositions. In one embodiment, the dried particles are collected on a filter, from which they can be removed for use in, e.g., medical applications. See Examples 1a and 1b and FIGS. 1A and 1B for illustrations of such a method and an apparatus that can be employed to perform it. In another embodiment, the spray-freeze atmosphere dried particles are collected in a product vessel. Partially dried particles may form a loose cake, from which remaining moisture can be removed by further atmospheric sublimation in a cold desiccated air stream, or they can optionally be removed to a lyophilizer or other suitable device and further dried under reduced pressure (below atmospheric pressure.)

Particles dried by any of the above methods exhibit substantially the same properties (e.g., particle size, porosity, and the like).

The atmospheric spray-freeze-drying process of the present invention, especially with vibration and/or internals, provides an economically feasible method of producing dried particles and increasing yield. Compositions prepared by the method can have properties that, e.g., facilitate respiratory administration. Unlike the spray-freeze-drying process disclosed in, e.g., U.S. Pat. No. 6,284,282 to Maa, this embodiment of the invention produces dried particles with a single apparatus. The atomization, freezing and drying of the present invention preferably occur in a single vessel, thus eliminating the need to transfer the sample, which may result in sample contamination and reduced yield. The entire operation can also be accomplished as a continuous operation, thus providing improved efficiency. By a "continuous operation" is meant that there is no temporal break between the steps and/or that there is no physical isolation (e.g., the frozen atomized particles are not removed to a separate container for drying). Other spray-freeze-dried processes utilized for preparing pharmaceutical compositions often include a second step of lyophilization, which involves removing the frozen particles from the spray-freezing chamber and transferring the particles to a lyophilizer. Such an additional step reduces the commercial feasibility of the spray-freeze-dry process and can result in agglomeration of the particles due to partial thawing of moisture entrapped in the particles.

Following the drying procedure, a composition of the invention can achieve the form of a free-flowing powder. The dry, porous particles of the composition are roughly the same size (geometric diameter) and shape as the frozen droplets prior to drying.

Dried particles of the invention exhibit desirable aerodynamic properties. Inertial impaction and gravitational settling of dried particles determines their deposition profile in the respiratory track of an animal. Methods of determining such deposition profiles are routine and conventional in the art. For example, the aerodynamic diameter is defined as the product of the actual particle diameter multiplied by the square root of the ratio of particle density to water density. ($d_{ae} = (sg)^{1/2} d_p$, $sg = \rho_{particle}/\rho_{water}$, $d_{ae}$ is particle aerodynamic diameter, $d_p$ is particle diameter).

Dried powders of the invention also exhibit other desirable properties. Examples 9 and 10 show some properties of compositions of insulin made by the methods of the invention. The particles show a desirable morphology (as shown by SEM) and a desirable density. Furthermore, the particles exhibit lower amounts of residual powder remaining in a delivery device following its use, exhibit greater stability than, e.g., liquid insulin formulations, and are readily reconstituted in liquid.

Compositions of the invention can be used to treat a variety of medical conditions. Among the many conditions that can be treated are diabetes, infectious diseases or any of the conditions that can be treated by the therapeutic agents discussed elsewhere herein, or by other therapeutic agents. In a preferred embodiment, compositions of the invention are vaccines.

One aspect of the invention is a method of treating a patient in need thereof, comprising administering to said patient an effective amount of a pharmaceutical composition produced by a method of the invention. By an "effective amount" is meant herein an amount that is effective to elicit a desired response. For example, an effective amount of an immunogenic composition is an amount that is effective to elicit a detectable immune response. An effective dose can be determined empirically, according to conventional procedures, taking into account well known factors such as the age, weight, and/or clinical condition of the patient, the method of and scheduling of administration, and the like. The patient can be any animal, preferably a mammal such as, e.g., a farm or other domestic animal, or a rat, mouse, hamster, guinea pig, rabbit, etc., preferably a human.

Compositions of the invention can be administered by any of a variety of routes that are known to the skilled worker, including, but not limited to, respiratory, intranasal, intrarectal, intravaginal, sublingual, oral or parenteral routes. In one embodiment, the composition is administered to a mucosal tissue, including, but not limited to, mucosal tissue of the nasal passages and the sinuses. In a preferred embodiment, a composition of the invention is administered to a patient in need thereof via the respiratory system. By "administration through the respiratory system" or "respiratory administration" is meant herein that an agent is administered through the nose (intranasally), after which the agent passes through the nasal cavities and the sinuses and, in some cases, into the lungs.

Conventional methods of administration may be used. Suitable applicators (e.g., inhalers) are known in the art. Typical delivery devices include, but are not limited to, the devices disclosed in U.S. Ser. Nos. 09/879,517 (filed Jun. 12, 2001) and 09/758,776 (filed Jan. 12, 2001). Dosages to be administered can be determined by conventional procedures known to those of skill in the art. See, e.g., *The Pharmacological Basis of Therapeutics*, Goodman and Gilman, eds., Macmillan Publishing Co., New York. Factors to be considered include the activity of the specific agent involved, the metabolic stability and length of action of the agent, mode and time of administration, drug combination, rate of excretion, the species being treated, and the age, body weight, general health, sex, diet and severity of the particular disease states of the host undergoing therapy. Dosages for eliciting an effective immune response (e.g., dosages for effective vaccination) are well known to those of skill in the art.

Another aspect of the invention is a method of treating a disorder (e.g., a condition or disease) by delivery of a therapeutic composition to a patient in need thereof, comprising administering to a mucosal membrane of the nasal and/or sinus passages of a patient a pharmaceutical composition of the invention. Another embodiment is a method of administering a therapeutic composition to a patient in need thereof, comprising administering to a mucosal membrane of the nasal and/or sinus passages of the patient a pharmaceutical composition of the invention. Another embodiment is a unit dosage receptacle or dry powder inhaler, comprising an effective amount of a pharmaceutical composition of the invention.

Compositions of the invention can achieve greater therapeutic effects following intranasal administration than do liquid formulations or other types of dry formulations, such as, e.g., spray-dried formulations. See, e.g., Examples 2 and 3. Therefore, the invention relates to a method of reducing the amount of a therapeutic agent that is required to produce an efficacious result following intranasal administration to a patient in need thereof, comprising administering to said patient, intranasally, an effective amount of a pharmaceutical composition of the invention.

In one aspect, the invention relates to a method to elicit an immune response in a patient, comprising administering to the patient an effective amount of an immunogenic composition of the invention. The term "immune response" as used herein encompasses, for example, mechanisms by which a multi-cellular organism produces antibodies against an antigenic material that invades the cells of the organism or the extra-cellular fluid of the organism. The antibody so produced may belong to any of the immunological classes, such as immunoglobulins A, D, E, G or M. Other types of responses, for example cellular and humoral immunity, are also included. Immune response to antigens is well studied and widely reported. A survey of immunology is given, e.g., in Roitt I., (1994). *Essential Immunology*, Blackwell Scientific Publications, London. Methods in immunology are routine and conventional (see, e.g., *Currents Protocols in Immunology*; edited by John E. Coligan et al., John Wiley & Sons, Inc.).

In one aspect, the invention relates to a vaccine (an agent used to stimulate the immune system of a living organism so that protection against future harm is provided). An influenza vaccine, for example, can protect a patient, at least to a finite degree, against infection by influenza. That is, the vaccine can result in the amelioration of at least some of the symptoms engendered by infection with the flu virus. A vaccine composition of the invention can take the form of, e.g., protein (such as in a subunit vaccine), viral particles, or DNA that encodes an antigen of interest.

Example 2 shows the preparation of a spray-freeze-dried (SFD) composition of the invention that comprises inactivated influenza viral particles. The example shows the use of a particular strain of influenza virus. One of skill in the art will recognize that other strains of influenza call also be used.

Most infectious agents enter the body and exert their pathophysiologic effects through mucous membranes. Protection against infection can be provided at the first site of entry by neutralizing infectious agents with locally produced mucosal IgA. Although systemic immune responses are readily elicited by traditional immunization routes (such as IM, ID, etc.), mucosal responses are more difficult to achieve in general. An advantage of intranasal (IN) delivery of dry powder vaccine is its ability to elicit both systemic and mucosal immune response. In addition, IN powder vaccine delivery may reduce the required dose because of the effectiveness of mucosal powder drug intake.

Example 2 shows that intranasal delivery of a spray-freeze-dried flu vaccine, which comprises an excipient, produces equivalent antibody production as does intramuscular delivery of a much larger dose of vaccine.

Example 3 shows that SFD inactivated influenza particles can elicit IgG and IgA responses, which are enhanced when chitosan is present as an excipient.

Example 4 shows influenza stability studies. The lyophilization process does not adversely after the stability of the particles, whereas milling of freeze-dried particles leads to dramatic decreases.

Examples 5-7 demonstrate the preparation and use of a DNA influenza vaccine. Methods of the present invention can be used to prepare and/or deliver vaccine compositions that comprise DNA molecules. Methods to engineer DNA vaccines, e.g., influenza vaccines, are well known in the art, as is discussed elsewhere herein. Example 5 illustrates a model system, in which DNA plasmids encoding the marker gene, firefly luciferase, are introduced into rats intranasally, in either liquid formulations, or dry (FD) formulations prepared according to methods of the invention. Luciferase gene expression is observed in nasal, but not lung, tissue. IN administration of the powder formulation results in comparable levels of gene expression as with liquid formulation. Examples 6 and 7 illustrate how to produce a DNA vaccine comprising an influenza haemagglutinin (HA) encoding sequence, and that such a vaccine elicits a significant response when inoculated into rats. An SFD formulation containing the excipient trehalose, prepared in accordance with the present invention and administered intranasally, elicits a stronger antibody response than does a comparable amount of a liquid formulation introduced intranaslly, or a formulation introduced intramuscularly.

Example 8 illustrates an immunization regimen in which, e.g., priming is performed with DNA encoding influenza haemagglutinin, and a boost with influenza viral particles follows. This regimen provides unexpectedly high antibody responses.

In another aspect, the invention relates to an inventive pharmaceutical composition for respiratory administration, comprising insulin, and to methods of making the composition and using it to treat a patient. Respiratory delivery of insulin provides several advantages, e.g., as compared to administration by intradermal or subdermal injection, including increased patient compliance and the elimination of the need for diabetic patients to administer frequent self injections. Some properties of insulin formulations of the invention are shown in Examples 9 and 10.

In Examples 2-10 presented herein, compositions are prepared by a spray-freeze-dry (lyophilized) method, sometimes referred to as "SFD." In the compositions of these examples, the particles have a mean average diameter of at least about 20 µm. These compositions are comparable to compositions prepared by a spray-freeze-atmosphere-dry method (Examples 1, 11 and 12), and thus the findings also apply to compositions prepared by the latter method. In the foregoing and in the following examples, all temperatures are set forth uncorrected in degrees Celsius; and, unless otherwise indicated, all parts and percentages are by weight.

EXAMPLES

Example 1

1a) A Method and Apparatus for Preparing Spray-Freeze-Atmosphere-Dried Pharmaceutical Compositions of the Invention Any of a variety of apparati can be used to produce a pharmaceutical composition of the invention. Referring to FIG. 1, a spray-freeze-atmospheric-drying apparatus that can be used in accordance with the present invention is generally shown at 10. An exemplary example of the method to produce an active pharmaceutical ingredient (API), e.g., one suitable for administration to the respiratory system, is as follows. A liquid feed line 12 is fluidly connected to an atomizing spray nozzle 14. A mixture of the API and a suitable liquid is disposed within the liquid feed line as will be explained further below. The spray nozzle 14 is disposed within a spray-freeze-atmospheric-drying chamber 16. In a preferred embodiment, a nebulizing line 18 (e.g., using compressed gas) interfaces with the spray nozzle 14 in order to atomize the mixture. Atomizing gases may include, e.g., nitrogen, oxygen, or air. Other conventional types of nozzles are also effective in generating the appropriate atomized particle size including a 2-fluid atomizer, a pressure atomizer, an ultrasonic nebulizer or even more preferably a vibrating orifice aerosol generator (VOAG), each known to generate more uniform particle size distribution. A cold liquid (e.g., nitrogen) or solid (e.g., dry ice) can be placed inside the drying chamber to aid the rapid freezing of the atomized droplets.

A cooling system 20 provides cold air to the drying chamber 16 to maintain a temperature within the chamber 16 generally between about −20° C. and −40° C. at the primary drying stage. The temperature within the drying chamber 16 is preferably maintained well below the freezing point of the mixture. The cold air is produced by redundant cooling chambers 22 that utilize liquid nitrogen, solid $CO_2$, or an equivalent cooling agent to produce the subfreezing temperatures. Redundant cooling chambers 22 provide the flexibility to maintain operation of the system even if one of the chambers 22 needs to be shut down. A cold air inlet line 24 provides the atmospheric freezing air to the drying chamber 16 from the cooling system 20. A cold air return line 26 receives the cold air from the drying chamber 16 and returns the cold air to the cooling system 20 to maintain circulation between the drying chamber 16 and the cooling chambers 22. A filter 28 is disposed inside the chamber 16 preferably between the nozzle 14 and the cold air return line 26. The filter 28 collects the spray-freeze-atmospheric-dried particles of the API from which the API may be recovered for future medical use.

A temperature controller 30 is disposed between the cooling system 20 and the drying chamber 16 in the cold air inlet line 24 to maintain the temperature of the cold air injected into the drying chamber 16 in the desirable range. A supplemental air filter 32 is disposed in the cold air outlet line 26 between the chamber 16 and the cooling system 20 to collect any residual material that may escape from the chamber 16 thereby preventing the material from contaminating the cooling system 20. Valves 34 are disposed in the cold air inlet and cold air outlet lines 24, 26 between the temperature controller 30 and the supplemental filter 32 respectively in order to seal off the drying chamber 16 for maintenance or other operational procedures.

A pump or blower 36 is disposed between the supplemental air filter 32 and the cooling system 20 in the cold air outlet line 26 to circulate cooling air through the cooling system 20 and a chamber 16. Inlet and outlet valves 38 are disposed at an inlet 40 and outlet 42 of each cooling chamber 22 enabling each cooling chamber 22 to be separately sealed off from the cold air circulation line 24, 26 for maintenance or other operational procedures. Additionally, a bypass valve 44 is disposed in a bypass valve line 46 fluidly connected between the cold air inlet line 24 and the cold air outlet line 26 in order to allow for circulation of the cooling air through the cooling system 20 when the chamber 16 is sealed off from the cooling system 20.

Because the spray nozzle 14 is disposed within the chamber 16, the nozzle's 14 operational temperature is below the freezing point of the mixture being provided to the spray nozzle 14. Therefore, the spray valve 14 has a tendency to freeze preventing the mixture from being atomized inside the chamber 16 in an appropriate manner. Thus, heating tape 48 is operatively connected to the valve 14 to maintain the valve at a temperature above the freezing point of the mixture. Other conventional methods of maintaining the spray nozzle 14 at a temperature above the freezing point of the mixture may be used as would be known to those of skill in the art.

During operation, the atomized API is introduced to the chamber 16 through the spray nozzle and is rapidly frozen by the cold air also being introduced to the chamber 16 from the cooling system 20. The air circulating within the chamber 16 will preferably maintain the particles in a fluidized state. While the particles are maintained in the fluidized state and, additionally, are collected in the filter 28, the circulating cooling air will dry the particles by removing the liquid that may be entrapped in the now solid particle, that have been frozen in the chamber 16. Continued circulation of the cooling air will reduce the moisture in each of the particles to a negligible amount. As primary drying is completed, the circulating gas can optionally gradually be increased to room temperature to facilitate secondary drying and reduced condensation during sample removal.

Preferably, the spray nozzle 14 will direct the atomized mixture toward the inlet cooling line 24 inside the chamber 16. However, it should be understood that the spray nozzle 14 may be directed toward the outlet cooling line 26 or any other side of the drying chamber 16 necessary to optimize the spray freeze atmospheric drying process. Further, the spray nozzle 14 may be selected to produce various atomized particle sizes as may be desired for any given API and delivery method.

Alternatively, the frozen and dried particles are optionally removed from the filter 28 and introduced to a lyophilizer or other suitable device, which operates at a reduced atmospheric pressure, wherein residual moisture is removed and the particles are thoroughly dried. The lyophilizer dehydrates the particles while the particles are maintained in a frozen state as the water passes from the solid phase directly to the vapor phase, as is known in the art.

Inclusion of a spray step in the spray-freeze-atmospheric-drying process allows for the processing of the solution to a dried particulate matter at about atmospheric pressure. The processing of the spray frozen substances at about atmospheric pressure provides for APIs that are readily aerosolized, and that are suitable for administration to a patient. In addition, the method as taught by the present invention provides an economical means of commercialization for producing suitable API's.

Figure 1A:
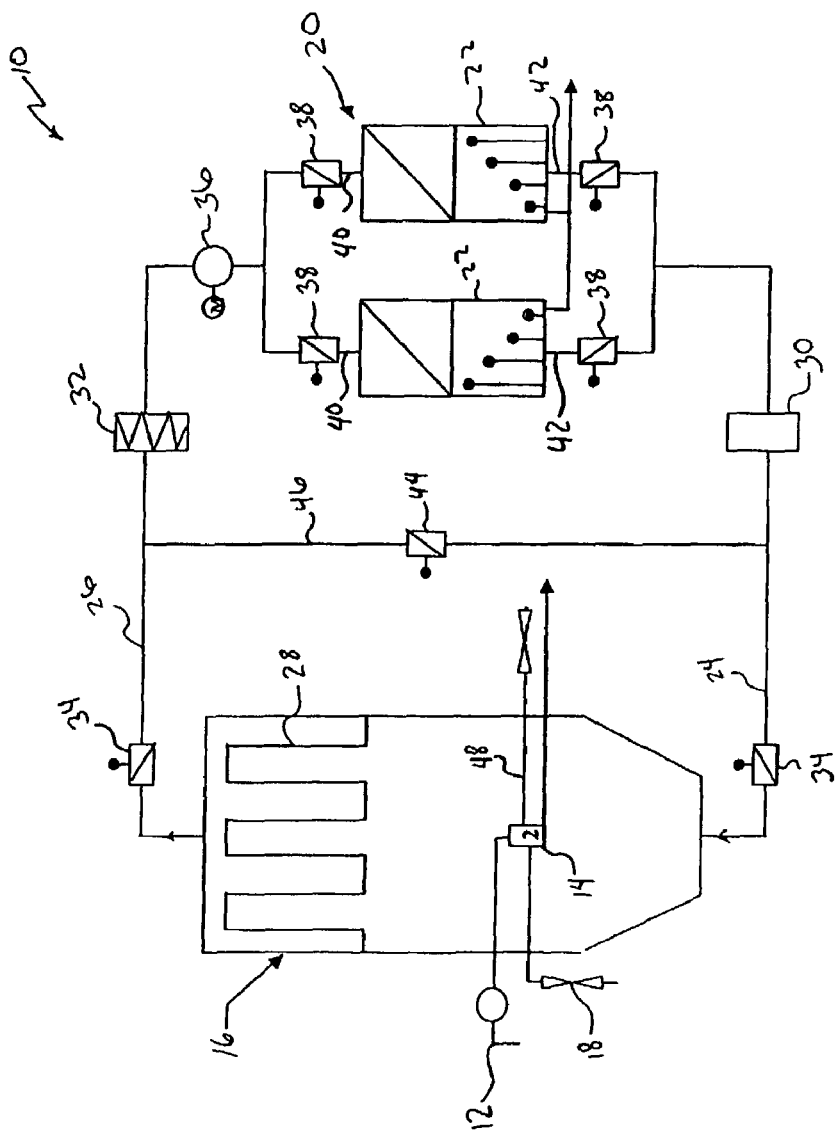
FIG. 1A shows a schematic view of a spray-freeze atmosphere dry apparatus of the invention.
Figure 1B:
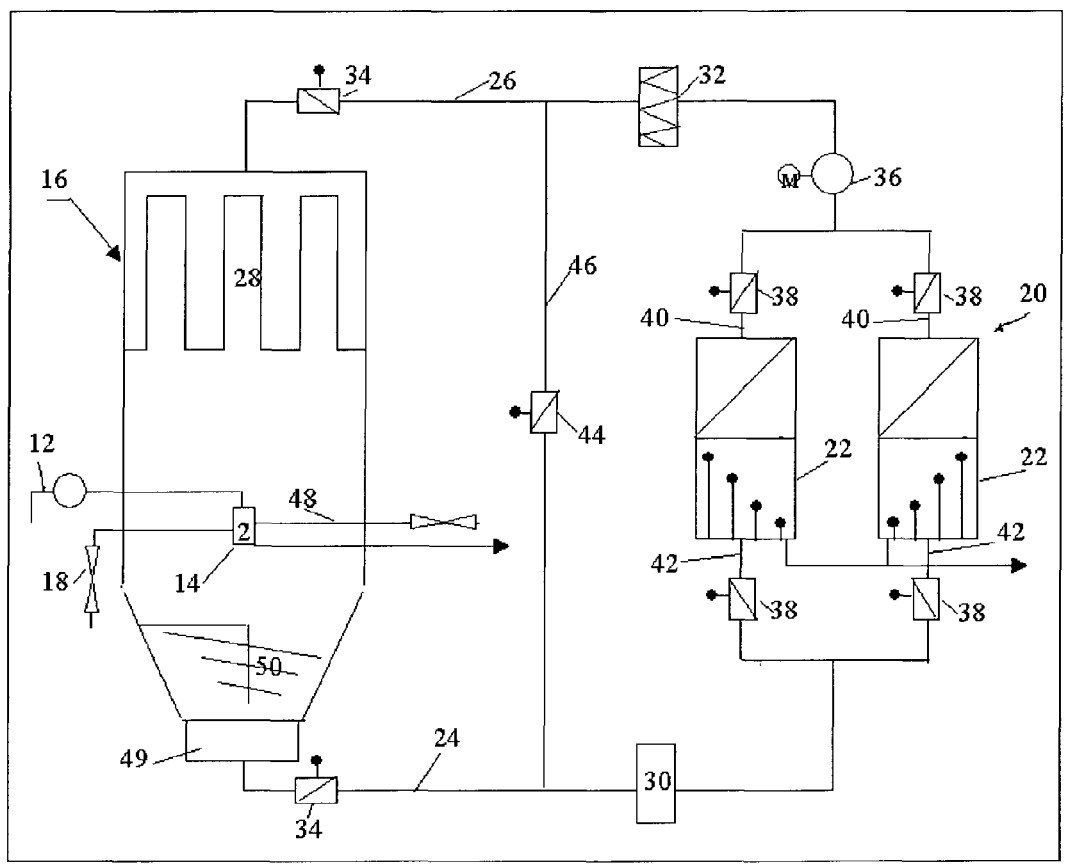
FIG. 1B shows a schematic view of a spray-freeze-drying set-up with Vibration and Internals.

1b) A Method and Apparatus for Preparing Spray-Freeze-Atmosphere-Dried Pharmaceutical Compositions of the Invention, Using a Vibrational Fluidized Bed with Internals A variant of the apparatus shown in FIG. 1A is shown in FIG. 1B. This variant comprises means for vibration (49) as well as special internals (50). The vibration and internals allow the solid, frozen particles to achieve a fluidized state as they are dried by sublimation in a cold desiccated air stream at about atmospheric pressure. This is especially useful when the frozen particles are sticky or cohesive, and is valuable in the powder cake building process when a sticky frozen powder is fluidized and elutriated.

To increase the product yield, a completely sealed system may be designed to keep frozen powder from escaping. A filter disc or paper filter disk or paper filter may be used to trap the powder elutriated from the fluidized bed below. Vibration, intervals, mechanical stirring, or combinations thereof are useful when a sticky frozen powder is fluidized and elutriated. As the sublimation proceeds, the frozen particles became porous (lighter) and the aerodynamic behavior changes. The partially dried particles may form a loose cake on exit at the disk filter, from which the remaining moisture may be removed, e.g., by sublimation at about atmospheric pressure, using a cold desiccated gas stream.

Similar to the method in Example 1a, the atomized API is introduced to the chamber 16 through the spray nozzle and is rapidly frozen by the cold air also being introduced to the chamber 16 from the cooling system 24 (see FIG. 1B). During operation, the vibrator 49 is turned on in an optimized frequency (0-100 Hz) and amplitude. The cold, dried fluidizing gas from cooling line 24 entering from the bottom of the chamber 16 fluidizes the frozen particles. Large particle agglomerates are broken under vibration as well as the assistance of special internals (static blades) 50 located inside chamber 16. Channeling normally occurring with cohesive powder is reduced or completely eliminated in such an operating condition. In most cases small frozen particles are easily elutriated and carried out by the fluidizing gas to the filter 28. A powder cake on the filter 28 is gradually built up in the fluidization and elutriation process.

A high flow-rate is available because of the use of a particle sealed system such as described and is recommended in the powder cake building process to increase the drying rate. A high flow-rate is also used in the drying process because the drying rate of frozen powder is much faster in a fixed bed state at high flow-rate than that in a slow fluidized bed state. The atmospheric spray-freeze-drying of the present invention with vibration and/or internals provides an economically feasible method of producing dried particles and increasing the yield.

Alternatively, a fast or circulating fluidized bed may be used in such a drying process if a higher drying rate is expected. A fast or circulating fluidized bed normally consists of a dense fluidized bed at the bottom and a dilute fluidized bed at the top as well as a powder returning system. In such a process, frozen particles are fluidized and carried by cold fluidizing air and collected by a cyclone at the top then returned to the dense fluidized bed through a specially designed powder valve. For easier cooling, an internal cyclone is preferred and the returned powder valve, which is specially designed with certain resistance, will only allow powder to come down rather than fluidizing air by pass. In order to break up the particle agglomerates and improve particle circulation, similar internals are also preferably used.

Alternatively, the frozen and dried particles are optionally removed from the filter and introduced to a lyophilizer or other suitable device, which operates at a reduced atmospheric pressure, wherein residual moisture is removed and the particles are thoroughly dried. The lyophilizer dehydrates the particles while the particles are maintained in a frozen state as the moisture passes from the solid phase directly to the vapor phase, as is known in the art.

The atmospheric spray-freeze-drying of the present invention with vibration and/or internals provides an economically feasible method of producing dried particles and increasing the yield.

Example 2

Nasal Delivery of Inactivated Influenza Virus Particles

Dry powder formulations of whole, inactivated, influenza virus A/PR/9/34 H1N1 particles were prepared in a spray-freeze dried batch process. A flu virus preparation was mixed into an aqueous solution, then atomized with a BD AccuSpray nozzle. Liquid particle size data were obtained with a Sympatech diffractometer measuring at approximately 2 inches from the nozzle tip. The median diameter of particles produced at these concentrations was approximately 50 microns. A typical particle size distribution produced by the BD AccuSpray nozzle is shown in FIG. 4. Liquid nitrogen was placed in a Virtis freeze-drying flask and the flask was positioned beneath the spray nozzle. The distance between the nozzle and liquid nitrogen was about three inches. The nebulized liquid droplets froze instantaneously upon contact with the liquid nitrogen. The flask was attached to a lyophilizer and immediately the excess liquid nitrogen was evaporated off. The frozen aerosols were typically dried within 48 hours and reached a moisture level below about 1 wt %.

In one experiment, testing was conducted to determine the strength of the immune response following intranasal (IN) or intramuscular (IM) delivery of various formulations of influenza vaccine. The study was conducted on rats and the following groups were evaluated:

Group 1 - IN. 100 ug of influenza* Ag in 50 µl volume of liquid.
Group 2 - IM injection. 100 µg of influenza* Ag in 50 µl volume of liquid
Group 3 - IN delivery. 100 µg influenza* Ag in 10 mg trehalose, freeze-dried powder
Group 4 - IN delivery. 100 µg influenza* Ag in 10 mg trehalose + chitosan, freeze-dried powder
Group 5 - IN delivery. 100 µg influenza* Ag in 10 mg trehalose + chitosan, spray-freeze-dried (SFD) powder
Group 6 - IN delivery. 10 mg freeze-dried trehalose only

*Inactivated whole Influenza virus A/PR/8/34 H1N1

Rats were immunized three times, at week 0, week 3, and week 6. Serum samples were collected at week 3, week 5 and week 8 and nasal lavage fluid was collected at week 8.

Subsequent to each delivery of flu vaccine, blood samples were taken to determine the magnitude of the immune response to the flu vaccine as measured by the antibody (Ab) response to the vaccine. Also determined was the amount of powder that was delivered during each vaccination. Conventional methods were used to determine factors such as the potency of immune response and the amount of powder delivered. FIG. 2 shows the serum Ab titers following each immunization. In summary, even though the serum Ab titers following IM delivery were cumulatively higher than those delivered by the intranasal deliveries, IN delivery of a spray freeze-dried flu vaccine was able to reach comparable levels of serum Ab response, in spite of low vaccine dose delivery (as low as 0-10% at the second immunization). In summary, this experiment suggests that with the full vaccine dose, IN delivery of spray freeze-dried flu vaccine is able to elicit comparable levels of serum Ab response as that of the IM group, and better responses than that of IN liquid group. As shown in Table 1, all IN flu vaccination groups are able to elicit positive nasal IgA response as contrast to negative nasal IgA titers following IM injection and an IN negative control. This study demonstrates that IN delivery of SFD flu vaccine is able to elicit both nasal mucosal responses and systemic immune responses.

TABLE 1

| | | Nasal IgA titers | | | |
|---|---|---|---|---|---|
| Group 1 (IN, liquid) | Group 2 IM | Group 3 IN, powder | Group 4 IN, chitosan | Group 6 SFD, chitosan | Group 7 IN Trehalose |
| 80 | <20 | <20 | 20 | 40 | <20 |
| 160 | <20 | 80 | 20 | 40 | <20 |
| 160 | <20 | <20 | 40 | 40 | <20 |
| 160 | <20 | 20 | 40 | | |

Example 3

Comparison of Serum and Nasal Mucosal Immune Responses Following IN Delivery of SFD Flu Vaccine with/without Chitosan This dose-ranging example compares immune responses of Brown Norway rats following IN delivery of SFD flu whole virus with and without chitosan. The following groups, each containing 4 rats, were evaluated:

1 - IN. 1 µg of flu* Ag in 5 mg trehalose, SFD
2 - IN. 1 µg of flu* Ag in 5 mg trehalose + chitosan, SFD
3 - IN. 10 µg of flu* Ag in 5 mg trehalose, SFD
4 - IN. 10 µg of flu* Ag in 5 mg trehalose + chitosan, SFD Inactivated whole Influenza virus strain A/PR/8/34 H1N1 was used in this example. The rats were immunized IN three times. The results, as shown in FIGS. 13A and 13B, indicate that a 10 µg dose of flu vaccine elicits stronger serum Ig and nasal IgA responses than does a dose of 1 µg, and that formulations with chitosan elicit a serum Ab response that is stronger than formulations without chitosan.

Example 4

Influenza Activity Studies

A series of experiments and milling processes affect influenza (flu) vaccine activity. A haemagglutinin assay (HA) was adopted in the studies as an indicator of influenza activity.

This assay tests HA titers of influenza vaccine based on the ability of influenza virus to haemagglutinate chicken red blood cells, an indicator of influenza vaccine potency. Briefly, two powder samples of inactivated influenza virus particles were prepared; the first was lyophilized, the second was lyophilized then milled. The sample was milled using a Wig-L-Bug ball micromill. This mill uses a one inch stainless steel vial with an endcap. The sample is placed into the vial along with a single stainless steel ball bearing, capped, and secured into position on the mill. The vial is vibrated from end to end at a rate that is variable for a prescribed time period. After milling, the sample is removed using a small spatula. Lyophilized and milled influenza powders were reconstituted back to original liquid influenza vaccine concentrations based on total protein concentration. The activity of reconstituted influenza vaccines was determined by comparing their HA titer to that of original influenza vaccine. The results are shown below:

| Original liquid flu vaccine | HA titer > 60 billion |
| Lyophilized flu vaccine | HA titer > 60 billion |
| Lyophilized and milled flu vaccine | HA titer = 4352 |
| Original liquid flu vaccine | HA titer > 60 billion |
| Spray-freeze-dried flu vaccine | HA titer > 60 billion |

These data indicate that the lyophilization process doesn't substantially affect vaccine activity in terms of HA titer. However, the milling process decreased HA titer dramatically. The same HA titer study was used to evaluate whether the SFD method would affect the activity of influenza vaccine. Influenza powder made by the SFD method was reconstituted back to original liquid influenza vaccine concentration based on total protein concentration. The activity of reconstituted influenza vaccines was determined by comparing their HA titer to that of original influenza vaccine.

The result demonstrates that the SFD method did not detrimentally affect influenza vaccine activity and that free-flowing influenza vaccine powder can be prepared, ready for administering, with full preservation of vaccine activity and without additional milling operation.

Example 5

IN Delivery of Plasmid DNA ("Naked DNA") Encoding Luciferase

Effective gene therapy and DNA-based immunization requires protein expression from the delivered gene. As such, reporter gene systems are commonly used as preliminary models for determining the feasibility of such therapies. This study evaluated luciferase activity following IN delivery of various DNA doses and formulations.

A. Liquid Formulation

A plasmid was used in which firefly luciferase-encoding sequences are placed under the control of a CMV promoter (pCMV-LUC). PCMV-LUC was obtained from Aldevron LLC, located at 3233 15$^{th}$ St. South, Fargo, N. Dak., 58104. A liquid formulation was prepared and doses of 50 µg or 100 µg in a volume of 50 µl in PBS were delivered IN to Brown Norway rats. Nasal and lung tissues were collected 24 hours after DNA delivery, homogenized and tested for luciferase activity using a luminescence assay.

FIG. 5 shows that luciferase activity was detected in nasal tissue, but not in lung tissue. IN delivery of 100 µg DNA resulted in higher luciferase activity than 50 µg of DNA.

B. Comparison of Liquid and Dry Powder Formulations

Liquid formulations of pCMV-LUC were prepared as described above. Dry powder (FD) formulations were prepared by lyophilization and milling as described in Example 4, using trehalose as an excipient. In some preparations, the excipient chitosan was also present. Doses of 100 µg in 50 µl of PBS of the liquid formulation, or 100 µg in 5 mg total powder for the powder formulations were administered to rats and samples were analyzed as above.

FIG. 6 shows that both dry powder and liquid formulations result in high luciferase activity in nasal tissue, but not in lung tissue. IN delivery of dry powder results in comparable levels of luciferase activity as that obtained with the liquid formulation This result indicates the feasibility of delivering DNA in the form of SFD powders.

Example 6

A DNA Influenza Vaccine

A plasmid was prepared, using conventional recombinant techniques, in which a DNA sequence encoding the influenza virus surface antigen haemagglutinin was placed under the control of CMVPro sequences of a CMV early promoter (Robinson et al. (1995) in *Vaccines* 95, Cold Spring Harbor Laboratory Press, Cold Spring Harbor, N.Y., pp. 69-75). The plasmid (pFLU-HA) was purified by conventional techniques and inoculated into rats by several methods: intra-muscular (IM), intranasal, liquid formulation (IN-liquid) and intranasal-SFD, with the excipient trehalose (IN-SFD-trehalose). The serum Ab response was measured. As shown in FIG. 3, IN delivery of SFD flu vaccine elicits serum Ab responses at least comparable to that of IM injection and higher responses than that of IN liquid delivery. IN SFD flu vaccination has shown its advantages over-conventional IM injection in this study.

Example 7

Immunization with DNA Influenza Vaccines

Based on the preliminary result from IN DNA powder delivery, as shown above, a larger scale study was conducted to compare immune response following various formulations of DNA vaccine. The pFLU-HA plasmid was prepared in a liquid formulation (in PBS) or in a dry powder formulation that optionally contained trehalose/chitosan. Two types of dry formulations were used: FD (standard freeze-dry formulation) and SFD (spray-freeze dry (lyophilized) formulation). Doses of 50 µg of plasmid DNA of each dry formulation were administered intranasally (IN), and a comparable dose of the liquid formulation was administered intramuscularly (IM) or IN to Brown Norway rats on days 0, 21 and 42. Serum samples were taken on days 21, 35 and 56, and nasal lavage was taken on day 56.

FIG. 7 shows that serum antibody titers following IN administration of the powder formulations were comparable to IM injection, and stronger than IN administration of the liquid formulation. The IN SFD/chitosan formulation elicits the strongest Ab response at the early stage of immunization. This suggests that an SFD/chitosan administration may allow for reduced vaccination doses and/or frequency of administration.

Table 2 shows that lack of nasal IgA responses in all experimental groups except a few animals from groups with IN SFD DNA delivery.

TABLE 2

Nasal IgA titers

|       | IM   | IN liquid | FD   | FD/chtsan | SFD  | SFD/chtsn |
|-------|------|-----------|------|-----------|------|-----------|
| Rat 1 | <10  | <10       | <10  | <10       | <10  | <10       |
| Rat 2 | <10  | <10       | <10  | <10       | <10  | <10       |
| Rat 3 | <10  | <10       | <10  | <10       | <10  | <10       |
| Rat 4 | <10  | <10       | <10  | <10       | <10  | <10       |
| Rat 5 | <10  | <10       | <10  | <10       | 10   | 10        |
| Rat 6 | <10  | <10       | <10  | <10       | <10  | 10        |
| Rat 7 | <10  | <10       | <10  | <10       | <10  | <10       |
| Rat 8 | <10  | <10       | <10  | <10       | <10  | <10       |
| Rat 9 |      |           | <10  | <10       | <10  | <10       |

The overall result from this study shows potential advantages of SFD/chitosan DNA formulation in eliciting better serum and nasal mucosal immune response in animal models.

Example 8

Flu DNA Primary Plus Viral Boost Regimen

A recently developed vaccination approach for numerous diseases, including HIV, is the so-called "prime-boost" approach, wherein the initial "priming" immunization and secondary "boosters" employ different vaccine classes (*Immunology Today* April 21(4), 163-165, 2000). For example, one may prime with a plasmid DNA version of the vaccine followed by a subsequent boost with a subunit protein, inactivated virus or vectored DNA preparation. This strategy was adopted in this study to investigate the potency of immune response when various formulations are delivered via different immunization routes and different combinations of immunization route.

pFLU-HA plasmid was prepared in liquid or dry formulations (FD, with and without trehalose/chitosan, and SFD, with and without trehalose/chitosan) as described in Example 5. These formulations were used for immunizations number 1 and 2 (primary immunizations).

For immunization number 3 (boost immunization), inactivated influenza was prepared in PBS (liquid formulation) or in trehalose/chitosan (dry powder formulation). Each group was divided into 2 subgroups: one received IM liquid influenza virus immunization and the other received IN influenza virus immunization of various formulations.

Brown Norway rats were immunized with selected formulations on days 0, 21 and 42. Serum samples were taken on days 21, 35 and 56, and nasal lavage, vaginal lavage and BAL were taken on day 56.

A summary of the vaccination regimens and the Ab responses observed is shown in Tables 3A through 3G. These data show that:
- DNA priming+influenza virus boost elicits a much stronger serum anti-influenza Ab titers than DNA or virus alone
- IN SFD/chitosan DNA priming+IM virus boost elicits a much stronger nasal IgA response than DNA or IM virus alone.
- IN SFD/chitosan DNA priming+IM virus boost elicits a stronger nasal IgA response than IN FD/chitosan DNA priming+IM virus boost.
- IN SFD/chitosan DNA priming+IM virus boost elicits a stronger nasal IgA response than the same strategy without chitosan
- IN SFD/chitosan DNA priming+IM virus boost elicits a stronger nasal IgA response than IN liquid DNA priming+IM virus boost
- Positive IgA and total Ig titers were detected in BAL fluid of all groups Table 3 (below) shows a trial with flu DNA priming followed by a viral boost. Table 3A shows flu DNA priming and boost trial: $1^{st}$ bleed serum total Ig titers (day 21). Table 3B shows flu DNA priming and boost trial: $2^{nd}$ bleed serum Ig titers (day 35). Table 3C shows flu DNA priming and boost trial: $3^{rd}$ serum total Ig titers (day 56). Table 3D shows flu priming and boost trial: Nasal IgA titers (day 56). Table 3E shows flu priming and boost trial: Vaginal IgA titers (day 56). Table 3F shows flu priming and boost trial: BAL IgA titers (day 56). Table 3G shows flu priming and boost trial: BAL total Ig titers (day 56).

As shown in Table 3A to 3C, powder groups in this study generally elicit stronger serum Ab titers than liquid groups. In addition, the strong nasal IgA responses following IN SFD/chitosan priming plus an IM boost (Table 3D, group 5a) are unexpected, given that neither DNA immunization alone, nor IM virus immunization alone, elicits a positive nasal IgA response. IN SFD DNA/chitosan primary plus an IM boost elicits a better immune response than IN DNA or IM virus alone.

TABLE 3A

| Group ID         | Group 1    | Group 2 | Group 3 | Group 4         | Group 5         |
|------------------|------------|---------|---------|-----------------|-----------------|
| Immunization 1 (DNA) | IN Liquid | IN FD   | IN SFD  | IN FD/ chitosan | IN SFD Chitosan |
| Rat 1            | <50        | 6400    | 51200   | 6400            | 6400            |
| Rat 2            | <50        | 12800   | 12800   | 3200            | 25600           |
| Rat 3            | 1600       | 6400    | 25600   | 6400            | 6400            |
| Rat 4            | 400        | 6400    | 12800   | 25600           | 25600           |
| Rat 5            | <50        | 800     | 6400    | 25600           | 3200            |
| Rat 6            | <50        | 25600   | 6400    | 12800           | 3200            |
| Rat 7            | 800        | 25600   | 12800   | 12800           | 12800           |
| Rat 8            | <50        | 12800   | 12800   | 6400            | 25600           |
| Rat 9            | 200        | 12800   | 12800   | 3200            | 25600           |
| Rat 10           | <50        | 12800   | 12800   | 12800           | 3200            |
| Avg. titers      | 300        | 12240   | 16640   | 11520           | 13760           |

TABLE 3B

| Group ID             | Group 1   | Group 2 | Group 3 | Group 4         | Group 5         |
|----------------------|-----------|---------|---------|-----------------|-----------------|
| Immunization 1 + 2 (DNA) | IN Liquid | IN FD   | IN SFD  | IN FD/ chitosan | IN SFD chitosan |
| Rat 1                | 400       | 12800   | 102400  | dead            | 12800           |
| Rat 2                | 400       | 51200   | 12800   | 12800           | 25600           |
| Rat 3                | 1600      | 6400    | 25600   | 51200           | 12800           |
| Rat 4                | <50       | 25600   | 25600   | 51200           | 51200           |
| Rat 5                | 200       | 1600    | 25600   | 6400            | 3200            |
| Rat 6                | 50        | 25600   | 51200   | 51200           | dead            |
| Rat 7                | 3200      | 12800   | 102400  | 12800           | 25600           |
| Rat 8                | <50       | 25600   | 12800   | dead            | dead            |
| Rat 9                | 1600      | 25600   | dead    | 25600           | dead            |
| Rat 10               | 200       | 25600   | 6400    | 102400          | 25600           |
| Avg. titers          | 765       | 21280   | 40533   | 39200           | 22400           |

TABLE 3C

| Group ID | Group 1A | Group 1B | Group 2A | Group 2B | Group 3A | Group 3B | Group 4A | Group 4B | Group 5A | Group 5B |
|---|---|---|---|---|---|---|---|---|---|---|
| Immunization 1 + 2 (DNA) | IN Liquid | IN liquid | IN FD | IN FD | IN SFD | IN SFD | IN FD/chitosan | IN FD/chitosan | IN SFD/chitosan | IN SFD/chitosan |
| Immunization 3 (virus) | IM | IN liquid | IM | IN FD | IM | IN SFD | IM | IN FD/chitosan | IM | IN SFD/chitosan |
| Rat 1 | 51200 | 25600 | 409600 | 819200 | 819200 | 819200 | dead | 409600 | 1638400 | dead |
| Rat 2 | 25600 | 102400 | 819200 | 819200 | 819200 | 1638400 | 1638400 | 409600 | 1638400 | 204800 |
| Rat 3 | 819200 | 25600 | 819200 | 819200 | 819200 | dead | 3276800 | dead | 1638400 | dead |
| Rat 4 | | 51200 | 409600 | 409600 | 819200 | 409600 | 3276800 | 819200 | 1638400 | dead |
| Rat 5 | 102400 | 12800 | 409600 | 819200 | 819200 | | 819200 | 819200 | 819200 | 102400 |
| Rat 6 | | | | | | 819200 | | | | |
| Avg. titers | 249600 | 43520 | 573440 | 737280 | 819200 | 955733 | 2252800 | 614400 | 1474560 | 153600 |

TABLE 3D

| Group ID | Group 1A | Group 1B | Group 2A | Group 2B | Group 3A | Group 3B | Group 4A | Group 4B | Group 5A | Group 5B |
|---|---|---|---|---|---|---|---|---|---|---|
| Immunization 1 + 2 (DNA) | IN liq. | IN liq | IN FD | IN FD | IN SFD | IN SFD | IN FD/chtsn | IN FD/chtsn | IN SFD/chtsn | IN SFD/chtsn |
| Immunization 3 (virus) | IM | IN liq. | IM | IN FD | IM | IN SFD | IM | IN FD/chtsn | IM | IN SFD/chtsn |
| Rat 1 | <10 | 20 | <10 | 40 | <10 | 160 | dead | 40 | 10 | dead |
| Rat 2 | <10 | 40 | <10 | 40 | <10 | 40 | <10 | 10 | 40 | 40 |
| Rat 3 | <10 | 40 | <10 | 20 | <10 | dead | <10 | dead | 40 | dead |
| Rat 4 | <10 | 20 | <10 | 40 | <10 | 40 | <10 | 40 | 20 | dead |
| Rat 5 | <10 | <10 | <10 | 40 | <10 | | <10 | 20 | <10 | 80 |
| Rat 6 | | | | | | <10 | | | | |
| Avg. titers | <10 | 24 | <10 | 36 | <10 | 80 | <10 | 27.5 | 22 | 60 |

TABLE 3E

| Group ID | Group 1A | Group 1B | Group 2A | Group 2B | Group 3A | Group 3B | Group 4A | Group 4B | Group 5A | Group 5B |
|---|---|---|---|---|---|---|---|---|---|---|
| Immunization 1 + 2 (DNA) | IN liq. | IN liq | IN FD | IN FD | IN SFD | IN SFD | IN FD/chtsn | IN FD/chtsn | IN SFD/chtsn | IN SFD/chtsn |
| Immunization 3 (virus) | IM | IN liq. | IM | IN FD | IM | IN SFD | IM | IN FD/chtsn | IM | IN SFD/chtsn |
| Rat 1 | <8 | <8 | <8 | <8 | 16 | <8 | dead | <8 | <8 | dead |
| Rat 2 | <8 | <8 | <8 | <8 | <8 | <8 | <8 | <8 | <8 | <8 |
| Rat 3 | <8 | <8 | <8 | <8 | <8 | dead | <8 | dead | <8 | dead |
| Rat 4 | <8 | <8 | <8 | <8 | <8 | <8 | <8 | <8 | <8 | dead |
| Rat 5 | <8 | <8 | <8 | <8 | <8 | | <8 | <8 | <8 | <8 |
| Rat 6 | | | | | | <8 | | | | |

TABLE 3F

| Group ID | Group 1A | Group 1B | Group 2A | Group 2B | Group 3A | Group 3B | Group 4A | Group 4B | Group 5A | Group 5B |
|---|---|---|---|---|---|---|---|---|---|---|
| Immunization 1 + 2 (DNA) | IN liq. | IN liq | IN FD | IN FD | IN SFD | IN SFD | IN FD/chtsn | IN FD/chtsn | IN SFD/chtsn | IN SFD/chtsn |
| Immunization 3 (virus) | IM | IN liq. | IM | IN FD | IM | IN SFD | IM | IN FD/chtsn | IM | IN SFD/chtsn |
| Rat 1 | 4 | 4 | 4 | 16 | 64 | 32 | dead | 16 | 16 | dead |
| Rat 2 | <1 | 4 | 4 | 4 | 4 | 16 | 4 | <1 | 32 | 8 |
| Rat 3 | 2 | 32 | <1 | 4 | 4 | dead | 2 | Dead | 4 | dead |
| Rat 4 | <1 | 16 | <1 | 4 | <1 | 16 | 16 | 16 | 16 | dead |
| Rat 5 | 2 | 4 | 2 | 2 | 2 | | 4 | <1 | 4 | 8 |
| Rat 6 | | | | | | 32 | | | | |

TABLE 3G

| Group ID | Group 1A | Group 1B | Group 2A | Group 2B | Group 3A | Group 3B | Group 4A | Group 4B | Group 5A | Group 5B |
|---|---|---|---|---|---|---|---|---|---|---|
| Immunization 1 + 2 (DNA) | IN liq. | IN liq | IN FD | IN FD | IN SFD | IN SFD | IN FD/chtsn | IN FD/chtsn | IN SFD/chtsn | IN SFD/chtsn |
| Immunization 3 (virus) | IM | IN liq. | IM | IN FD | IM | IN SFD | IM | IN FD/chtsn | IM | IN SFD/chtsn |
| Rat 1 | 64 | 32 | 256 | 256 | 4096 | 128 | Dead | 128 | 512 | Dead |

TABLE 3G-continued

| Group ID | Group 1A | Group 1B | Group 2A | Group 2B | Group 3A | Group 3B | Group 4A | Group 4B | Group 5A | Group 5B |
|---|---|---|---|---|---|---|---|---|---|---|
| Rat 2 | 32 | 128 | 256 | 256 | 2048 | 1024 | 256 | 32 | 1024 | 256 |
| Rat 3 | 256 | 32 | 256 | 512 | 256 | | 256 | Dead | 128 | Dead |
| Rat 4 | 8 | 64 | 256 | 128 | 512 | 512 | 1024 | 128 | 1024 | Dead |
| Rat 5 | 64 | 8 | 64 | 256 | 128 | | 512 | 256 | 512 | 32 |
| Rat 6 | | | | | 1024 | | | | | |
| Avg. titers | 85 | 53 | 218 | 282 | 1344 | 555 | 512 | 136 | 640 | 144 |

Example 9

Insulin and Insulin with an Excipient by SD and SFD

Summarized in Table 4 are experimentally determined physical characteristics of spray-dried and spray freeze-dried insulin compositions in combination with a lactose excipient. During the formation of these compositions the outlet temperature of the solution being sprayed from the atomizer was also monitored along with percent yield and tap density (g/cm$^3$) of the particles. The samples and tabulated data are indicated below:

TABLE 4

| Solution | Process | Tap Density (grams per centimeter cubed) |
|---|---|---|
| Pure Insulin | Spray dried | .29 |
| 40/60: Insulin/Lactose | Spray dried | .49 |
| Pure Insulin | Spray freeze dried (SFD) | 0.01 |
| 40/60: Insulin/Lactose | Spray freeze dried (SFD) | 0.06 |

As is depicted in the table, the tap densities of spray freeze-dried essentially pure insulin and the 40/60 solution of insulin/lactose were significantly lower than those of spray-dried insulin and insulin/lactose particles. The SFD powder compositions possessed better retention of protein stability and bioactivity than spray dried compositions. In contrast, spray-dried pure insulin and insulin/lactose (40/60) powders were significantly denser, having tap densities of 0.29 and 0.49 g/cm$^3$. Although not wishing to be bound by any particular theory, applicants believe that these advantages ensue because spray-freeze-drying takes place at a much lower temperature (roughly 100° C. lower) than conventional spray-drying.

A 2% by weight solution of insulin in water and a 5% by weight of insulin/lactose (40/60) were processed by a spray freeze-dry (lyophilization) procedure of the invention. The resulting porous particles exhibited aerosol characteristics suitable for delivery into the respiratory system of an animal. Applicants' testing has indicated that the smallest aerodynamic particle size obtained with the spray freeze drying method consisted of excipient-free insulin, i.e., essentially pure insulin. However, it is understood to be within the scope of the invention that formulations consisting of insulin and excipient are suitable for the intended purpose of administering to the respiratory system. In addition, the SFD insulin particles (FIG. 19) showed virtually no detectable hydration when exposed to ambient conditions (20° C., 53% RH) for 15 minutes and during storage compared to spray-dried insulin/lactose particles. In contrast, FIG. 20 shows the retained morphology of the SFD insulin/lactose particles after exposure to the same ambient conditions for 15 minutes. Typically, SFD insulin/lactose particles pick up at least 2 to 5 wt % moisture upon exposure to relative humidity>50% These results indicate that SFD porous insulin produced by the methods of the invention possess relatively high resistance to ambient moisture compared to SFD porous insulin/lactose.

Another desired attribute provided for by the methods taught in the instant invention is the substantial reduction of residual powder remaining in the delivery device after use. The percent admitted dose from a particular delivery device is calculated gravimetrically. By way of example, API's prepared in accordance with the methods of the instant invention when used in conjunction with delivery devices such as those disclosed in U.S. patent application Ser. Nos. 09/879,517 filed Jun. 12, 2001 and 09/758,776, filed Jan. 12, 2001 resulted in less than 5% residual power remaining in the delivery device. By comparison, approximately 20 wt % of spray dried powder remained in the same delivery device. In addition, aerosolization of the SFD powders was visually observed to be efficient and left essentially no residual powder in the respiratory delivery devices. Photographs of drug carrier capsules from this device with SD (lower left capsule) and SFD (upper right capsule) powders after rupturing the capsule membranes are shown in FIG. 21, which clearly demonstrates excellent aerosol properties of SFD powders.

Example 10

Stability of SFD Insulin Powder vs. Liquid Insulin

The stability of the SFD insulin was evaluated relative to U500 Liquid Lilly Humulin-R with m-cresol, a standard liquid insulin widely being administered today. SFD pure insulin and insulin/trehalose were tested for eight weeks at 40° C. and 75% relative humidity. Pure insulin was also tested while sealed in an aluminum overwrap. The liquid insulin was tested at 25° C. (room temperature) and 60% relative humidity. The percentage of Desamido formation relative to the sample was measured to determine the stability of each sample. The percent formation of Desamido was determined initially, at one week, at two weeks, at four weeks, at six weeks, and at eight weeks.

Desamido is known to adversely affect diabetic patients by producing an immunity in the patient to insulin. The FDA has issued limits to the amount of desamido content in insulin to less than 10%.

The SFD pure insulin proved to be exceptionally stable throughout the eight week evaluation. The results for SFD pure insulin were:

| | Initial | 1 week | 2 weeks | 4 weeks | 6 weeks | 8 weeks |
|---|---|---|---|---|---|---|
| % Desamido | 0 | 0.329 | 0 | 0.222 | 1.015 | 2.66 |

The SFD pure insulin sample that was wrapped with aluminum exhibited chemical stability throughout the eight week trial period. Until the six week evaluation, the amount of desamido detected was below the statistical error and was considered negligible. The amount of desamido detected peaked at the six week evaluation at 0.75%. The results for SFD pure insulin with the aluminum overwrap were as follows:

| | Initial | 1 week | 2 weeks | 4 weeks | 6 weeks | 8 weeks |
|---|---|---|---|---|---|---|
| % Desamido | 0 | 0.396 | 0.12 | 0 | 1.752 | 0.750 |

SFD insulin was evaluated with Trehalose excipient. In this case, no desamido was detected until week 6. Overall, the addition of Trehalose significantly improved the shelf life of the SFD insulin. The results indicate:

| | Initial | 1 week | 2 weeks | 4 weeks | 6 weeks | 8 weeks |
|---|---|---|---|---|---|---|
| % Desamido | 0 | 0 | 0 | 0 | 0.24 | 1.57 |

The base line liquid insulin was also evaluated over 8 weeks to determine the amount of desamido growth. The liquid insulin proved to be much less stable relative to the SFD insulin over the eight week evaluation period. In addition to the weekly testing conducted, the liquid insulin was also evaluated at 24 and 72 hours. No desamido growth was detected at these early evaluations. A significant variable to the study is that the liquid insulin was evaluated at much less severe storage conditions than was the SFD insulin. Additionally, the liquid insulin included the chemical preservative m-cresol to slow the growth of the desamido.

| | Initial | 1 week | 2 weeks | 4 weeks | 6 weeks | 8 weeks |
|---|---|---|---|---|---|---|
| % Desamido | 0 | 1.216 | 1.23 | 1.32 | 1.640 | 2.13 |

Each of the SFD insulin samples proved to be significantly more stable than the liquid insulin. The liquid insulin degraded significantly faster than the SFD powder formulation. The SFD insulin with the aluminum overwrap proved to be the most stable sample tested through the eight week trial at 40° C. at 75% relative humidity. The results indicate that the SFD powder insulin is much more stable than presently commercially available liquid insulin formulations.

FIG. 10 shows the growth rate of desamido of the SFD pure insulin tested against the liquid insulin.

Example 11

Vibrational Fluidized-Bed Spray Freeze Drying

Spray-freeze-dried, porous particles were successfully produced at about atmospheric pressure (no vacuum) in the presence of intervals and vibration, as described elsewhere herein. The internals and vibration-assisted fluidization were shown to enhance the sublimation of frozen aerosol. A 20 wt % mannitol solution (FIG. 11) (i.e. 80 wt % moisture) was dried at −20° C. in less than 40 minute to reach at 0.3 wt %. This is superior to, e.g., the results obtained by Leuenberger (U.S. Pat. No. 4,608,764).

The moisture content and drying time of 20 wt % mannitol (as a function of drying gas velocity) is shown in FIG. 11. The lowest drying curve presented in the table was generated in BDT where the rest of the data were extracted from the literature (Leuenberger, U.S. Pat. No. 4,608,764). Based on the result from TGA, the residual moisture was about 0.3% after 40-minute drying at gas velocity of 2 m/s. The morphology of the particles is shown to be porous as indicated by the SEM as shown in FIG. 12. The spray frozen aerosol below 20 μm exhibited strong cohesive force between particles and the fluidization gas could simply channel upward through the bed. When the spray frozen powder was dried at 0.39 m/s, −20° C. without internal and vibration, it was found that 95 wt % of powder remained at the bottom of the bed due to channeling after drying for three hours. The channeling in the fluidized-bed resulted poor drying efficiency. Roughly 5 wt % of powder elutriated to the top (after drying for three hours) of the bed and was dried at much faster rate than the powder collected from the bottom of the bed. Elutriation is the process by which fine particles are carried out by fluidizing gas from a fluidized bed when gas superficial velocity is higher than particle/agglomerate terminal velocity. The effect of drying gas velocity and elutriation in a fluidized-bed is explained in Example 13 from mass transfer analysis. The moisture levels of the samples collected from top and bottom at various time points are shown in FIG. 14. Only 5% of spray frozen powders elutriated to the top of the drying bed. 95% of frozen powder remained at the bottom; the poor drying efficiency was due to channeling. The powders elutriated to the top of the bed (collected by filter disc) were sampled at 30 and 60 minutes, and are shown by SEM in FIGS. 15 and 16. Powder collected at 60 minutes did not appear to be drier than the powder collected at 30 minutes. The newly elutriated, partially dried powders were mixed in with the drier powders and caused the agglomeration of the particles after samples were taken out. With the aid of internals and vibration, all powder elutriated to the top of fluidized bed to form a uniform cake thus eliminated channeling and provided efficient drying. As shown in FIG. 17 higher drying gas velocity, 2 m/s, the 20 wt % mannitol was dried to porous powder (0.3 wt % residual moisture) at much higher rate than the lower drying gas velocity, 0.39 m/s. The figure shows the effect of flow-rate on sublimation time in a vibrational fluidized-bed SFD process. With vibration and internals, all of the powder elutriated to the top of the drying bed. A high flow rate resulted in faster drying time and thus higher efficiency.

Example 12

Mass Transfer Analysis of the Drying Process in a Fluidized Bed and a Fixed Bed Dryer The terminal settling velocity of a 20 μm particle is about 0.012 m/s $$\left(\text{velocity} = \frac{\rho_p d_p^2 g}{18\mu}\right),$$

which corresponds when elutriation occurs for a single frozen particle. At such low gas flow rate (low Reynolds number) the mass transfer coefficient is very low. Richardson and Szekely (1961) have established an empirical equation below to correlate the mass transfer coefficient, k, with the Reynolds number for a gas-solid fluidized-bed.

$$Sh=0.37Re^{1.8} \quad 0.1<Re<15,$$

where Sh is Sherwood number ($=kd_p/D$), k is mass transfer coefficient, D is diffusion coefficient, $d_p$ is particle size), Re is Reynolds number ($=\rho_g u\, d_p/\mu$).

If particle agglomerate size $d_a=200$ μm, nitrogen density 1.29 kg/m³, viscosity of nitrogen fluid $1.81\times10^{-5}$ kg/m/s (Pa*s), fluid velocity 0.012 m/s (the terminal velocity of single particles at 20 μm. At the fluidizing gas velocity higher than the terminal velocity of single particles, the single particles derived from the collision and attrition of agglomerates in fluidized bed will be carried away or elutriated), (Re=0.171) then Sh is $1.54\times10^{-2}$.

At drying gas velocity greater than 0.012 m/s, the particles (20 μm or smaller) will elutriate out of the fluidized-bed and need to be collected by a filter or a cyclone. The operations by Leuenberger and BDT are far beyond the terminal velocity of the particles and a filter disc collects the powders as the cold dry gas stream continuously dries the frozen powders. In effect, the wet-frozen powders are elutriated and form a uniform cake at the top exit of the fluidized bed. As the drying gas is flowing through at high speed, the drying process is similar to that of a fixed-bed dryer. The mass transfer in a fixed bed can also be calculated from another empirical equation proposed by Ranz (1952) Chem. Eng. Prog. 48, 247:

$$Sh = 2.0 + 1.8 Sc^{\frac{1}{3}} Re^{\frac{1}{2}}$$

where Sc is Schmidt number ($=\mu/\rho_g D$). At high Re, for example, if particle size is 20 μm, nitrogen density 1.29 kg/m², viscosity of nitrogen fluid $1.81\times10^{-5}$ kg/m/s, fluid velocity 2.0 m/s (60 liter per minute in our experiment, pressure of source nitrogen 40 psi), then the Sh is calculated to be 4.7. By comparing the mass transfers between gas and solids in a fluidized bed at low Re and a fixed bed at high Re, the ratio of mass transfers in two situations is about 1:300.

In one set of experiments, the drying nitrogen velocity was at 0.03 m/s to dry 5 wt % PEG solution (95% moisture). At this flow rate, there were some powders elutriated (and collected by filter paper). However, no "powder" was observed on the filter paper since these frozen particles were not fully dried yet and thawed out as they deposited on the filter paper. The fluidized frozen sample collected at the bottom of the bed (truly fluidized) after 4 hours still contained 93% moisture. This observation supports our Sherwood number analysis that slow fluidization gives rise to poor mass transfer (drying) rate.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated by reference.

What is claimed is:

1. A method of preparing a pharmaceutical composition, comprising
   atomizing a liquid formulation of a therapeutic agent to produce an atomized formulation,
   freezing said atomized formulation to form solid particles, and
   drying said solid particles at about atmospheric pressure to produce dried particles, wherein said drying is performed in the presence of vibration, internals, mechanical stirring, or a combination thereof.

2. The method of claim 1, wherein said frozen, solid particles are in a fluidized state as they are being dried.

3. The method of claim 1, wherein said dried particles have a volume mean diameter of between about 35 μm and about 300 μm.

4. The method of claim 1, wherein said dried particles have a volume mean diameter of between about 50 μm and about 100 μm.

5. The method of claim 3, wherein at least about 50% of said dried particles have a volume diameter within about 80% of the mean.

6. The method of claim 1, wherein said dried particles have an average mean aerodynamic diameter of between about 8 μm and about 140 μm.

7. The method of claim 1, wherein said dried particles have an average mean aerodynamic diameter of between about 20 μm and about 70 μm.

8. The method of claim 1, wherein said freezing is performed by introducing said atomized formulation into a fluid or medium having a temperature below the freezing point of said liquid formulation.

9. The method of claim 8, wherein said fluid or medium has a boiling point or sublimation point lower than that of said atomized formulation.

10. The method of claim 8, wherein said fluid is a gas.

11. The method of claim 8, wherein said fluid is a liquid.

12. The method of claim 1, further comprising drying said dried particles by-lyophilization.

13. The method of claim 1, wherein said particles are dried in the presence of a flowing stream of gas.

14. The method of claim 1, wherein said atomizing, freezing and drying are carried out in a continuous process.

15. The method of claim 1, wherein said atomizing, freezing and drying are carried out in a single vessel.

16. The method of claim 1, wherein said therapeutic agent is a protein, a nucleic acid or a virus particle.

17. The method of claim 1, wherein said therapeutic agent is an immunogenic agent.

18. The method of claim 17, wherein said immunogenic agent is an influenza vaccine.

19. The method of claim 18, wherein said influenza vaccine comprises inactivated influenza virus particles or a nucleic acid encoding an influenza haemagglutinin protein, which is operatively linked to a CMV promoter.

20. The method of claim 1, wherein said therapeutic agent is insulin.

21. The method of claim 2, wherein said liquid formulation comprises a mucoadhesive.

22. The method of claim 21, wherein said mucoadhesive is chitosan, dermatan sulfate. chondroitin, or pectin.

23. The method of claim 1, wherein said liquid formulation of said therapeutic agent consists essentially of said therapeutic agent and water.

* * * * *